(12) United States Patent
Long et al.

(10) Patent No.: US 10,835,314 B2
(45) Date of Patent: Nov. 17, 2020

(54) METHOD AND APPARATUS FOR RAPID AND SAFE PULMONARY VEIN CARDIAC ABLATION

(71) Applicant: Farapulse, Inc., Menlo Park, CA (US)

(72) Inventors: Gary Long, Cincinnati, OH (US); Raju Viswanathan, Mountain View, CA (US)

(73) Assignee: Farapulse, Inc., Menlo Park, CA (US)

( * ) Notice: Subject to any disclaimer, the term of this patent is extended or adjusted under 35 U.S.C. 154(b) by 553 days.

(21) Appl. No.: 15/484,969

(22) Filed: Apr. 11, 2017

(65) Prior Publication Data

US 2017/0215953 A1 Aug. 3, 2017

Related U.S. Application Data

(63) Continuation of application No. PCT/US2015/055105, filed on Oct. 12, 2015.

(Continued)

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 2017/00477* (2013.01);
(Continued)

(58) Field of Classification Search
CPC ........... A61B 2018/00351; A61B 2018/00363; A61B 2018/00375; A61B 2018/00642;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Supplementary European Search Report for European Application No. 15733297.4, dated Aug. 10, 2017, 7 pages.

(Continued)

*Primary Examiner* — Michael F Peffley
*Assistant Examiner* — Bo Ouyang
(74) *Attorney, Agent, or Firm* — Cooley LLP

(57) ABSTRACT

An apparatus includes a shaft, the shaft including a plurality of stepped sections along the length of the shaft. The apparatus further includes a plurality of electrodes disposed along the length of the shaft, each electrode characterized by a geometric aspect ratio of the length of the electrode to the outer diameter of the electrode. Each electrode is located at a different stepped section of the plurality of stepped sections of the shaft and includes a set of leads. Each lead of the set of leads is configured to attain an electrical voltage potential of at least about 1 kV. The geometric aspect ratio of at least one electrode of the plurality of electrodes is in the range between about 3 and about 20.

17 Claims, 27 Drawing Sheets

Related U.S. Application Data

(60) Provisional application No. 62/122,152, filed on Oct. 14, 2014.

(51) Int. Cl.
  *A61B 17/00* (2006.01)
  *A61B 18/00* (2006.01)
  *A61M 25/01* (2006.01)

(52) U.S. Cl.
  CPC .............. *A61B 2017/00876* (2013.01); *A61B 2018/00351* (2013.01); *A61B 2018/00363* (2013.01); *A61B 2018/00375* (2013.01); *A61B 2018/00642* (2013.01); *A61B 2018/00827* (2013.01); *A61B 2018/00839* (2013.01); *A61B 2018/00875* (2013.01); *A61B 2018/00892* (2013.01); *A61B 2018/124* (2013.01); *A61B 2018/1405* (2013.01); *A61B 2018/1435* (2013.01); *A61M 25/0127* (2013.01)

(58) Field of Classification Search
  CPC ...... A61B 2018/143; A61B 2018/1467; A61B 2018/1475
  See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,558,091 A | 9/1996 | Acker et al. |
| 5,578,040 A | 11/1996 | Smith |
| 5,617,854 A | 4/1997 | Munsif |
| 5,624,430 A | 4/1997 | Eton et al. |
| 5,662,108 A | 9/1997 | Budd et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A * | 2/1999 | Fleischman ......... A61B 18/1492 606/33 |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,913,854 A * | 6/1999 | Maguire ............ A61B 18/1492 606/41 |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A * | 7/2000 | Webster, Jr. ....... A61B 18/1492 600/374 |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |

(56) References Cited

U.S. PATENT DOCUMENTS

| | | |
|---|---|---|
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,282,057 B2 | 10/2007 | Surti et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |

(56) References Cited

U.S. PATENT DOCUMENTS

| | | |
|---|---|---|
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,788,885 B2 | 10/2017 | Long et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,117,701 B2 | 11/2018 | Davalos et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,292,755 B2 | 5/2019 | Arena et al. |
| 10,322,286 B2 | 6/2019 | Viswanathan et al. |
| 10,342,598 B2 | 7/2019 | Long et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,531,914 B2 | 1/2020 | Stewart et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1* | 11/2002 | Bowe ............... A61B 18/1492 600/374 |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1* | 10/2007 | Keenan ............... A61N 1/05 600/374 |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0004661 A1 | 1/2010 | Verin et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |

(56) References Cited

U.S. PATENT DOCUMENTS

| | | |
|---|---|---|
| 2010/0191112 A1 | 7/2010 | Demarais et al. |
| 2010/0191232 A1* | 7/2010 | Boveda .................. A61B 18/14 606/33 |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0208185 A1* | 8/2011 | Diamant ............ A61B 18/1492 606/42 |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1* | 11/2011 | Morgan ................ A61B 18/042 606/45 |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1* | 3/2012 | Fish ........................ A61F 2/958 623/1.12 |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1* | 7/2014 | Clark .................... A61B 5/6885 600/424 |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1* | 4/2015 | Fischell ............ A61B 5/04001 600/381 |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |

(56) References Cited

U.S. PATENT DOCUMENTS

| | | |
|---|---|---|
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0214195 A1 | 8/2018 | Fraasch et al. |
| 2018/0214202 A1 | 8/2018 | Howard et al. |
| 2018/0221078 A1 | 8/2018 | Howard et al. |
| 2018/0235496 A1 | 8/2018 | Wu et al. |
| 2018/0243558 A1 | 8/2018 | Athos et al. |
| 2018/0250508 A1 | 9/2018 | Howard |
| 2018/0256109 A1 | 9/2018 | Wu et al. |
| 2018/0280080 A1 | 10/2018 | Govari et al. |
| 2018/0289417 A1 | 10/2018 | Schweitzer et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0038171 A1 | 2/2019 | Howard |
| 2019/0046791 A1 | 2/2019 | Ebbers et al. |
| 2019/0060632 A1 | 2/2019 | Asirvatham et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0209238 A1 | 7/2019 | Jimenez |
| 2019/0223938 A1 | 7/2019 | Arena et al. |
| 2019/0223948 A1 | 7/2019 | Stewart et al. |
| 2019/0223950 A1 | 7/2019 | Gelbart et al. |
| 2019/0231421 A1 | 8/2019 | Viswanathan et al. |
| 2019/0231425 A1 | 8/2019 | Waldstreicher et al. |
| 2019/0233809 A1 | 8/2019 | Neal, II et al. |
| 2019/0254735 A1 | 8/2019 | Stewart et al. |
| 2019/0256839 A1 | 8/2019 | Neal, II et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0350649 A1 | 11/2019 | Sutermeister et al. |
| 2019/0376055 A1 | 12/2019 | Davalos et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |
| 2020/0046423 A1 | 2/2020 | Viswanathan et al. |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |

(56) References Cited

FOREIGN PATENT DOCUMENTS

| | | |
|---|---|---|
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 97/24073 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2017/093926 | 6/2017 |
| WO | WO 2017/120169 | 7/2017 |
| WO | WO 2017/192477 | 11/2017 |
| WO | WO 2017/192495 | 11/2017 |
| WO | WO 2017/201504 | 11/2017 |
| WO | WO 2017/218734 | 12/2017 |
| WO | WO 2018/005511 | 1/2018 |
| WO | WO 2019/133606 | 7/2019 |

OTHER PUBLICATIONS

Office Action for U.S. Appl. No. 15/201,997, dated Aug. 29, 2017, 12 pages.
Office Action for U.S. Appl. No. 15/334,646, dated Jul. 25, 2017, 19 pages.
International Search Report and Written Opinion for International Application No. PCT/US2017/012099, dated May 18, 2017, 17 pages.
Office Action for U.S. Appl. No. 15/334,646, dated Nov. 16, 2017, 26 pages.
First Office Action for Chinese Application No. 201580006848.8, dated Jan. 29, 2018, 8 pages.
Office Action for European Application No. 15701856.5, dated Dec. 11, 2017, 6 pages.
Office Action for U.S. Appl. No. 15/795,062, dated Dec. 19, 2017, 14 pages.
Office Action for U.S. Appl. No. 15/795,075, dated Feb. 6, 2018, 9 pages.
Office Action for U.S. Appl. No. 15/796,255, dated Jan. 10, 2018, 12 pages.
Extended European Search Report for European Application No. 15806855.1, dated Jan. 3, 2018, 8 pages.
Extended European Search Report for European Application No. 15806278.6, dated Feb. 9, 2018, 5 pages.
Office Action for U.S. Appl. No. 15/796,375, dated Jan. 24, 2018, 25 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/499,804, dated Jan. 3, 2018, 20 pages.
Office Action for U.S. Appl. No. 15/794,717, dated Feb. 1, 2018, 10 pages.
Office Action for U.S. Appl. No. 15/795,062, dated Apr. 9, 2018, 20 pages.
Extended European Search Report for European Application No. 15849844.4, dated May 3, 2018, 8 pages.
Office Action for U.S. Appl. No. 15/711,266, dated Feb. 23, 2018, 14 pages.
Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Office Action for U.S. Appl. No. 15/201,997, dated Apr. 3, 2017, 6 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
International Search Report and Written Opinion for International Application No. PCT/US2015/031086, dated Oct. 21, 2015, 16 pages.
International Search Report and Written Opinion for International Application No. PCT/US2015/055105, dated Mar. 1, 2016, 15 pages.

(56) References Cited

OTHER PUBLICATIONS

International Search Report and Written Opinion for International Application No. PCT/US2015/035582, dated Oct. 2, 2015, 17 pages.
International Search Report and Written Opinion for International Application No. PCT/US2015/035592, dated Oct. 2, 2015, 13 pages.
International Search Report and Written Opinion for International Application No. PCT/US2016/057664, dated Feb. 24, 2017, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for European Application No. 13827672.0, dated Feb. 5, 2018, 6 pages.
Extended European Search Report for European Application No. 19182099.2, dated Dec. 13, 2019, 7 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/917,194, dated Apr. 29, 2019, 10 pages.
Office Action for U.S. Appl. No. 15/917,194, dated Dec. 20, 2019, 10 pages.
Notice of Reasons for Rejection for Japanese Application No. 2016-544072, dated Oct. 1, 2018, 11 pages.
Office Action for U.S. Appl. No. 15/201,983, dated Apr. 3, 2019, 16 pages.
Office Action for U.S. Appl. No. 15/201,983, dated Nov. 15, 2019, 15 pages.
Office Action for U.S. Appl. No. 15/354,475, dated May 23, 2019, 7 pages.
Office Action for U.S. Appl. No. 15/970,404, dated Oct. 9, 2018, 21 pages.
Office Action for U.S. Appl. No. 15/970,404, dated Apr. 12, 2019, 20 pages.
Office Action for U.S. Appl. No. 15/970,404, dated Nov. 12, 2019, 19 pages.
International Search Report and Written Opinion for International Application No. PCT/US2019/028943, dated Sep. 17, 2019, 17 pages.
International Search Report and Written Opinion for International Application No. PCT/US2019/030882, dated Sep. 10, 2019, 17 pages.

* cited by examiner

US 10,835,314 B2

METHOD AND APPARATUS FOR RAPID AND SAFE PULMONARY VEIN CARDIAC ABLATION

CROSS REFERENCE TO RELATED APPLICATIONS

This application is a continuation of International Application No. PCT/US2015/055105, filed Oct. 12, 2015, which claims the benefit of and priority to U.S. Provisional Application Ser. No. 62/122,152, entitled "METHOD AND APPARATUS FOR RAPID AND SAFE PULMONARY VEIN CARDIAC ABLATION" and filed Oct. 14, 2014, the disclosures of which are incorporated herein by reference in their entirety.

BACKGROUND

The embodiments described herein relate generally to medical devices for therapeutic electrical energy delivery, and particularly to systems and methods of high voltage electrical energy delivery in the context of ablating tissue rapidly and selectively by the application of pulsed voltage waveforms to produce exogenous electric fields to cause irreversible electroporation of tissue with the aid of suitably positioned catheter devices with multiple electrodes.

In the past two decades, the technique of electroporation has advanced from the laboratory to clinical applications, while the effects of brief pulses of high voltages and large electric fields on tissue has been investigated for the past forty years or more. Application of brief, high DC voltages to tissue, thereby generating locally high electric fields typically in the range of hundreds of Volts/centimeter, can disrupt cell membranes by generating pores in the cell membrane. While the precise mechanism of this electrically-driven pore generation (or electroporation) is not well understood, it is thought that the application of relatively large electric fields generates instabilities in the lipid bilayers in cell membranes, causing the occurrence of a distribution of local gaps or pores in the membrane. If the applied electric field at the membrane is larger than a threshold value, the electroporation is irreversible and the pores remain open, permitting exchange of material across the membrane and leading to necrosis and/or apoptosis (cell death). Subsequently the tissue heals in a natural process.

Some known processes of adipose tissue reduction by freezing, also known as cryogenically induced lipolysis, can involve a significant length of therapy time. In contrast, the action of irreversible electroporation can be much more rapid. Some known tissue ablation methods employing irreversible electroporation, however, involve destroying a significant mass of tissue, and one concern is the temperature increase in the tissue resulting from this ablation process.

While pulsed DC voltages are known to drive electroporation under the right circumstances, known approach do not provide for ease of navigation, placement and therapy delivery from one or more devices and for safe energy delivery, especially in the context of ablation therapy for cardiac arrhythmias with epicardial catheter devices.

Thus, there is a need for devices that can effectively deliver electroporation ablation therapy selectively to tissue in regions of interest while minimizing damage to healthy tissue. In particular, there is a need for devices that can efficiently deliver electroporation therapy to desired tissue regions while at the same time minimizing the occurrence of irreversible electroporation in undesired tissue regions. Such elective and effective electroporation delivery methods with enhanced safety of energy delivery can broaden the areas of clinical application of electroporation including therapeutic treatment of a variety of cardiac arrhythmias.

SUMMARY

An apparatus includes a shaft, the shaft including a plurality of stepped sections along the length of the shaft. The apparatus further includes a plurality of electrodes disposed along the length of the shaft, each electrode characterized by a geometric aspect ratio of the length of the electrode to the outer diameter of the electrode. Each electrode is located at a different stepped section of the plurality of stepped sections of the shaft and includes a set of leads. Each lead of the set of leads is configured to attain an electrical voltage potential of at least about 1 kV. The geometric aspect ratio of at least one electrode of the plurality of electrodes is in the range between about 3 and about 20.

DETAILED DESCRIPTION

Figure 1:
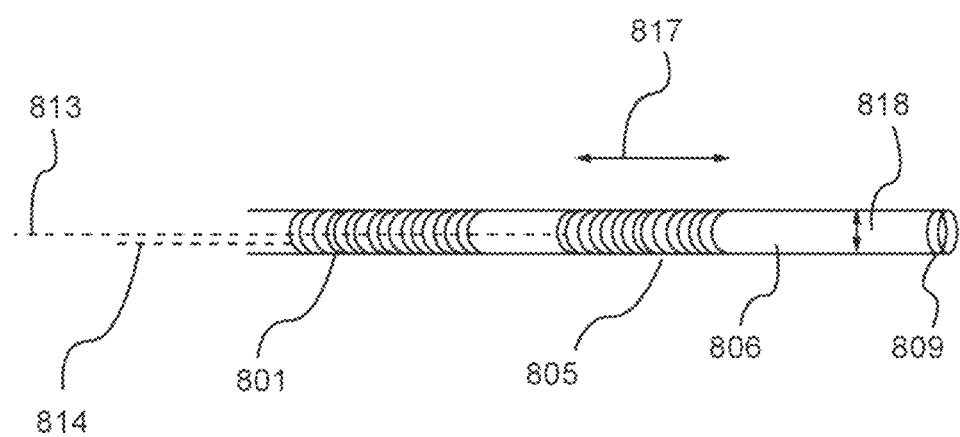
FIG. 1 is a schematic illustration of a catheter with a multiplicity of flexible electrodes disposed along its shaft, with an electrical lead attached to the inner surface of each electrode, and with a magnetic member located near the distal end of the catheter, according to embodiments.

In some embodiments, a system includes a generator unit configured for generating pulses, and a controller unit operably coupled to the generator unit, the controller unit configured for triggering the generator unit to generate one or more pulses. The system also includes a set of pacing leads operably coupled to the controller unit, the controller unit, the generator unit, and the set of pacing leads configured for driving the one or more pulses through the pacing leads. The system also includes at least two medical devices including a first medical device and a second medical device, each medical device operably coupled to the controller unit, each medical device including a plurality of electrodes. The controller unit is further configured for selecting one or more first electrodes from the plurality of electrodes of the first medical device and from the plurality of electrodes of the second medical device as cathodes for applying the one or more pulses. The controller unit is further configured for selecting one or more second electrodes from the plurality of electrodes of the first medical device and from the plurality of electrodes of the second medical device as anodes for applying the one or more pulses.

In some embodiments, a device includes a primary catheter, including one or more electrodes disposed in an intermediate portion of the primary catheter and one or more electrodes disposed in a distal portion of the primary catheter. The primary catheter also includes two or more channels configured for passage of secondary catheters, each channel continuous from a proximal portion of the primary catheter to a lateral exit position on the primary catheter, and one or more magnetic members disposed in the intermediate portion of the primary catheter. The primary catheter also includes and a magnetic member disposed in the distal portion of the primary catheter. The device further includes at least two secondary catheters configured for passage through the primary catheter device, each secondary catheter including one or more electrodes in its respective distal portion, and a magnetic member in its respective distal portion. The device also includes, for each electrode of the primary catheter and each electrode of the secondary catheter, an electrical lead attached to the corresponding electrode, each lead configured for, during use, being at an electrical voltage potential of at least 1 kV without resulting in dielectric breakdown of the two or more channels of the primary catheter. A geometric aspect ratio of at least one of the electrodes of the primary catheter device is in the range between about 3 and about 20.

In some embodiments, a system includes a pulse generator unit configured to generated voltage pulses, and a controller unit operably coupled to the pulse generator unit. The controller unit is configured for triggering the pulses of the generator unit and for applying voltages of one polarity to a set electrodes of a first medical device and voltages of an opposite polarity to a set electrodes of a second medical device. The system also includes a set of pacing leads operably coupled to the controller unit, the controller unit further configured for driving pacing signals through the pacing leads. The system also includes a primary catheter and a secondary catheter operably coupled to the controller unit, the primary catheter including a first set of electrodes, the secondary catheter including a second set of electrodes. The controller unit is configured for driving voltages through any electrode of the first set of electrodes and second set of electrode. The controller unit is further configured for selecting a sequence of pairs of electrodes from the first set of electrodes and the second set of electrodes. For each pair of electrodes, an electrode of the pair of electrodes has an opposite polarity from the other electrode of the pair of electrodes, and an electrode of the pair of electrodes selected from the primary catheter, the other electrode of the pair of electrodes selected from the secondary catheter. The controller unit is further configured for sequential application of voltage pulse trains over the sequence of pairs of electrodes.

In some embodiments, a method includes epicardially inserting two primary catheters, each primary catheter including a first set of electrodes disposed along its length. The method also includes positioning the primary catheters in conjoined form so as to substantially wrap around the pulmonary veins epicardially in a single contour. The method also includes passing a secondary catheter through each primary catheter, each secondary catheter extending out from a lateral side of its corresponding primary catheter. Each secondary catheter includes a second set of electrodes. The method also includes, for each secondary catheter, wrapping the secondary catheter around a portion of a pulmonary vein, and attaching the secondary to an intermediate portion or distal portion of its corresponding primary catheter, such that the secondary catheter epicardially encircles the pulmonary vein with a series of electrodes selected from the first set of electrodes of its corresponding primary catheter, from the second set of electrodes of the secondary catheter, or both. The method also includes selecting a set of pairs of electrodes from the first set of electrodes of the primary catheters and from the second set of electrodes of the secondary catheters, each electrode of each pair of electrodes having a cathode or an anode assignment. The method also includes recording electrocardiogram (ECG) signals from at least some electrodes of the first set of electrodes of the primary catheters and the second set of electrodes of the secondary catheters. The method further includes identifying refractory intervals in at least one ECG signal and, in at least one subsequent refractory interval, sequentially applying voltage pulse trains to the set of pairs of electrodes.

An apparatus includes a catheter shaft, and a set of flexible electrodes disposed along the length of the catheter shaft. Each flexible electrode is characterized by a geometric aspect ratio of the length of the flexible electrode to the outer diameter of the flexible electrode. Each flexible electrode includes a set of conducting rings separated by spaces and disposed along the catheter shaft. The set of conducting rings of each flexible electrode are electrically connected together so as to electrically define a common electrical potential for the each electrode. The catheter shaft includes gaps configured for separating adjacent flexible electrodes of the set of flexible electrodes. The apparatus also includes electrical leads attached to each of the flexible electrodes, each electrical lead configured for attaining an electrical voltage potential of at least 1 kV. The geometric aspect ratio of at least one of the flexible electrodes is in the range between about 3 and about 20

The terms "about" and "approximately" when used in connection with a referenced numeric indication means the referenced numeric indication plus or minus up to 10% of that referenced numeric indication. For example, the language "about 50" covers the range of 45 to 55.

As used in this specification, the singular forms "a," "an" and "the" include plural referents unless the context clearly dictates otherwise. Thus, for example, the term "an electrode" is intended to mean a single electrode or a plurality/combination of electrodes.

Any of the catheter devices described herein can be similar to the ablation catheters described in PCT Publication No. WO2014/025394, entitled "Catheters, Catheter Systems, and Methods for Puncturing Through a Tissue Structure," filed on Mar. 14, 2013 ("the '394 PCT Application), which is incorporated herein by reference in its entirety.

Aspects disclosed herein are directed to catheters, systems and methods for the selective and rapid application of DC voltage to drive irreversible electroporation. Catheter devices with flexible electrodes and methods for using a multiplicity of such devices for rapid and effective ablation of cardiac tissue are disclosed. In some embodiments, the irreversible electroporation system described herein includes a voltage/signal generator and a controller capable of being configured to apply voltages to a selected multiplicity or a subset of electrodes, with anode and cathode subsets being selected independently on distinct medical devices. The controller is additionally capable of applying control inputs whereby selected pairs of anode-cathode subsets of electrodes can be sequentially updated based on a pre-determined sequence.

FIG. 1 is a schematic illustration of a catheter with a multiplicity of flexible electrodes disposed along its shaft, with an electrical lead attached to the inner surface of each electrode, and with a magnetic member located near the distal end of the catheter. The catheter shaft 801 has a multiplicity of electrodes disposed along an extensive length of catheter at least about 5 cm in extent. For clarity, FIG. 1 shows two flexible electrodes 801 and 805 in the form of a coil wound around the catheter shaft; in some embodiments, the number of electrodes can be in the approximate range from two to six. Each electrode attaches to a lead, so that in FIG. 1 electrodes 801 and 805 respectively attach to leads 814 and 813.

Further, the distal tip region of the catheter has a magnetic member 809. The magnetic member 809 can be in the form of a magnetizable or ferromagnetic material, or it may be a magnetized object, with the poles of the magnetized object being either along a straight line or not. In some embodiments, at least one of the poles of the magnet represents a local magnetization direction that is substantially aligned with the longitudinal axis of the catheter.

In one embodiment the metallic, flexible coiled electrodes could comprise biocompatible metals such as titanium, platinum or platinum alloys. The catheter shaft is made of a flexible polymeric material such as for example Teflon, Nylon or Pebax.

In some embodiments, all the electrodes of a catheter have the same polarity, in which case the need for high dielectric strength material separating the leads is not a significant constraint, and the catheter can be relatively small in diameter, for instance being in the range of about 9 French, about 8 French or even about 6 French. Likewise, a higher voltage can be applied to the electrodes of the catheter as there is no risk of dielectric breakdown; in some instances, this could enhance the efficacy of irreversible electroporation ablation. The flexible electrode has a length 817 (denoted by L) associated with it, and its diameter 818 corresponds to the catheter diameter (denoted by d). The aspect ratio L/d of each flexible electrode is a geometric characteristic associated with the flexible electrode. In some embodiments, the aspect ratio of at least one of the flexible electrodes on the device is at least about 3, and at least in the range between about 3 and about 20, and in the range between about 5 and about 10 in some embodiments.

Figure 2:
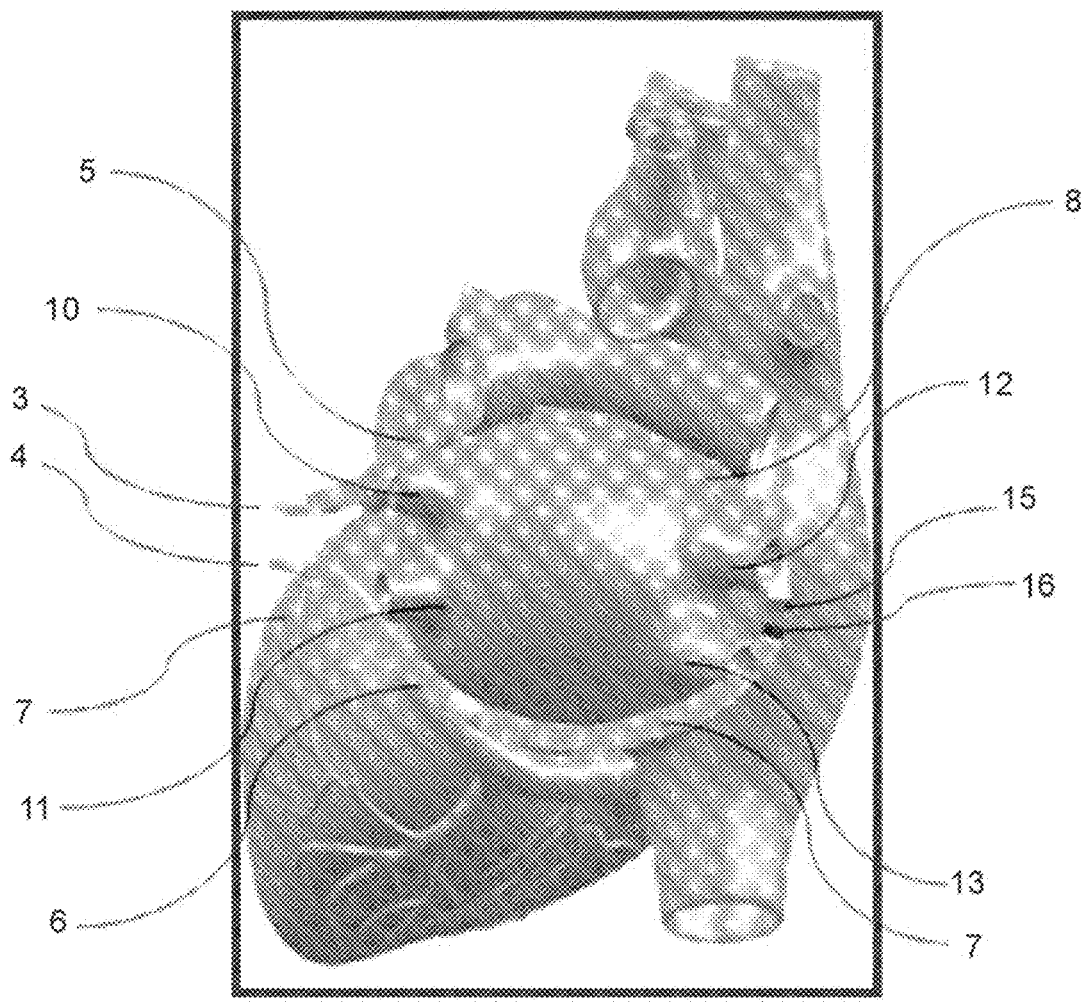
FIG. 2 is an illustration showing two catheters, each with multiple flexible electrodes disposed along its shaft and wrapped around a portion of the pulmonary veins of the heart in a subject body, with the distal ends of the two catheters in close proximity, according to embodiments. The two catheters together constitute an approximately closed contour around the pulmonary veins and each catheter positioned in the epicardial space around the heart.

FIG. 2 shows a pair of Pulmonary Vein isolation (PV isolation) ablation catheter devices, a first device with proximal end 3 and distal end 15, and a second device with proximal end 4 and distal end 16, each with a multiplicity of flexible electrodes disposed along its length. The first catheter device has two flexible electrodes labeled 5 and 8 disposed along its length, while the second catheter device has two flexible electrodes labeled 6 and 7. Each catheter is wrapped in the epicardial space around a portion of the pulmonary veins 10, 11, 12 and 13 of a heart 7 in a subject or patient anatomy, with the proximal portions 3 and 4 of the respective catheters extending out and away to eventually emerge from the patient's chest. In some embodiments the distal ends 15 and 16 of the two catheters have magnetic members that can aid in alignment of the two catheters. A puncturing apparatus using a subxiphoid pericardial access location and a guidewire-based delivery method to accomplish the placement of a multi-electrode catheter around the pulmonary veins was described in PCT Patent Application WO2014025394; the same method can be used to deliver and position the two catheters in FIG. 2. After the ends 3 and 4 of the two respective catheters extend and emerge out of the patient chest they can be cinched together to effectively hold the catheters in place or in stable positions relative to each other.

A voltage for electroporation can be applied to subsets of electrodes identified as anodes and cathodes respectively on the two catheters on approximately opposite sides of the closed contour defined by the shapes of the catheters around the pulmonary veins. The voltage is applied in brief pulses sufficient to cause irreversible electroporation and can be in the range of 0.5 kV to 10 kV, in the range from about 0.75 kV to about 2.5 kV, and all values and subranges in between, so that a threshold electric field value of about 200 Volts/cm is effectively achieved in the cardiac tissue to be ablated. In some embodiments, the marked or active electrodes on the two catheters can be automatically identified, or manually identified by suitable marking, on an X-ray or fluoroscopic image obtained at an appropriate angulation that permits identification of the geometric distance between anode and cathode electrodes, or their respective centroids. In one embodiment, the voltage generator setting for irreversible electroporation is then automatically identified by the electroporation system based on this distance measure. In some embodiments, the voltage value is selected directly by a user from a suitable dial, slider, touch screen, or any other user interface. The voltage pulse results in a current flowing between the anode and cathode electrodes on opposite sides of the contour defined by the conjoint shapes of the two catheters, with said current flowing through the cardiac wall tissue and through the intervening blood in the cardiac chamber, with the current entering the cardiac tissue from the anode electrodes and returning back through the cathode electrodes. For the configuration shown in FIG. 2, the forward and return current paths (leads) are respectively inside distinct catheters, since all active electrodes on a given catheter are of like polarity. Areas of cardiac wall tissue where the electric field is sufficiently large for irreversible electroporation are ablated during the voltage pulse application.

Figure 3:
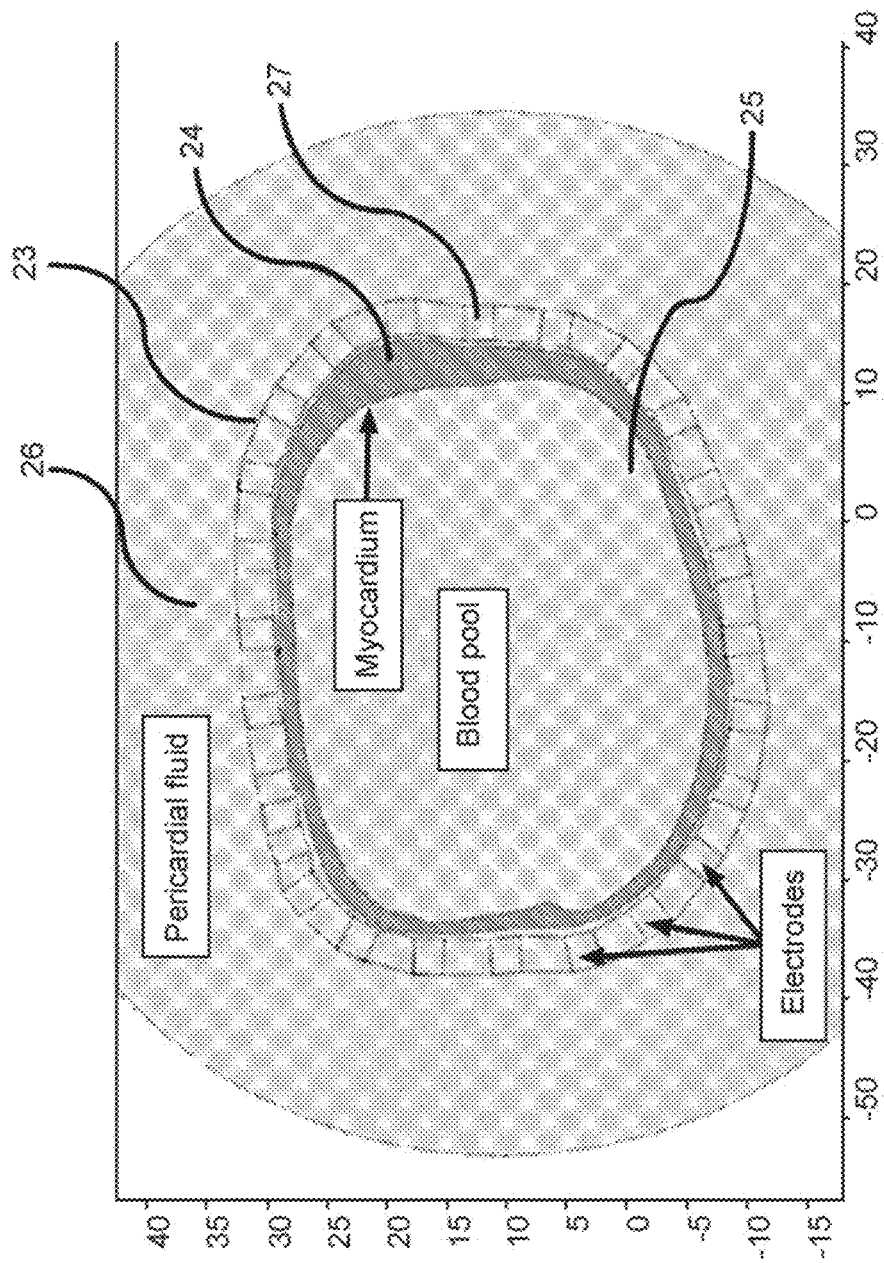
FIG. 3 is a schematic of a two dimensional model of a cardiac atrium, with various regions such as a myocardium disposed around an interior region of blood pool, a ring of electrodes around the myocardium, and pericardial fluid in an external region.

A two dimensional model of a cardiac atrium, with various regions such as a myocardium disposed around an interior region of blood pool, a ring of electrodes around the myocardium representing a catheter shaft, and pericardial fluid in an external region is shown in FIG. 3, with which simulation results can be obtained based on realistic values of electrical material properties for the various regions. A ring of electrodes 23 comprising a series of cells is disposed around a myocardium 24 which itself encircles a blood pool region 25. An external pericardial fluid region 26 surrounds the ring of electrodes. For purposes of simulation, individual electrode cells such as 27 can be defined or set to be either metal electrodes or insulation (representing catheter shaft regions that do not have electrodes) in terms of electrical properties.

Figure 4:
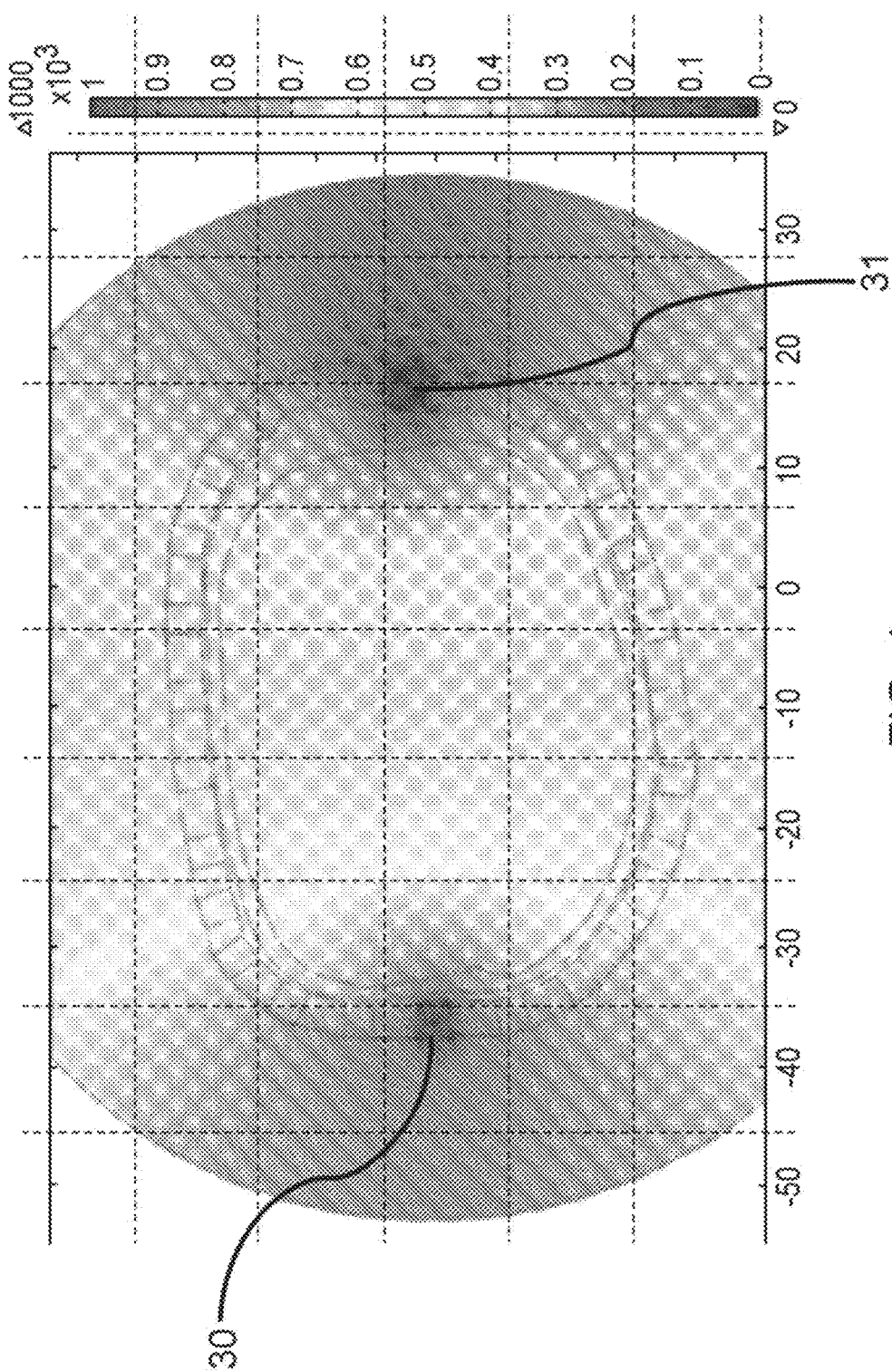
FIG. 4 is a simulation result in the form of a shaded contour plot of the electric potential, with a voltage difference set between two electrodes on opposite sides of the myocardium and all other electrodes replaced by insulation, according to embodiments.
Figure 5:
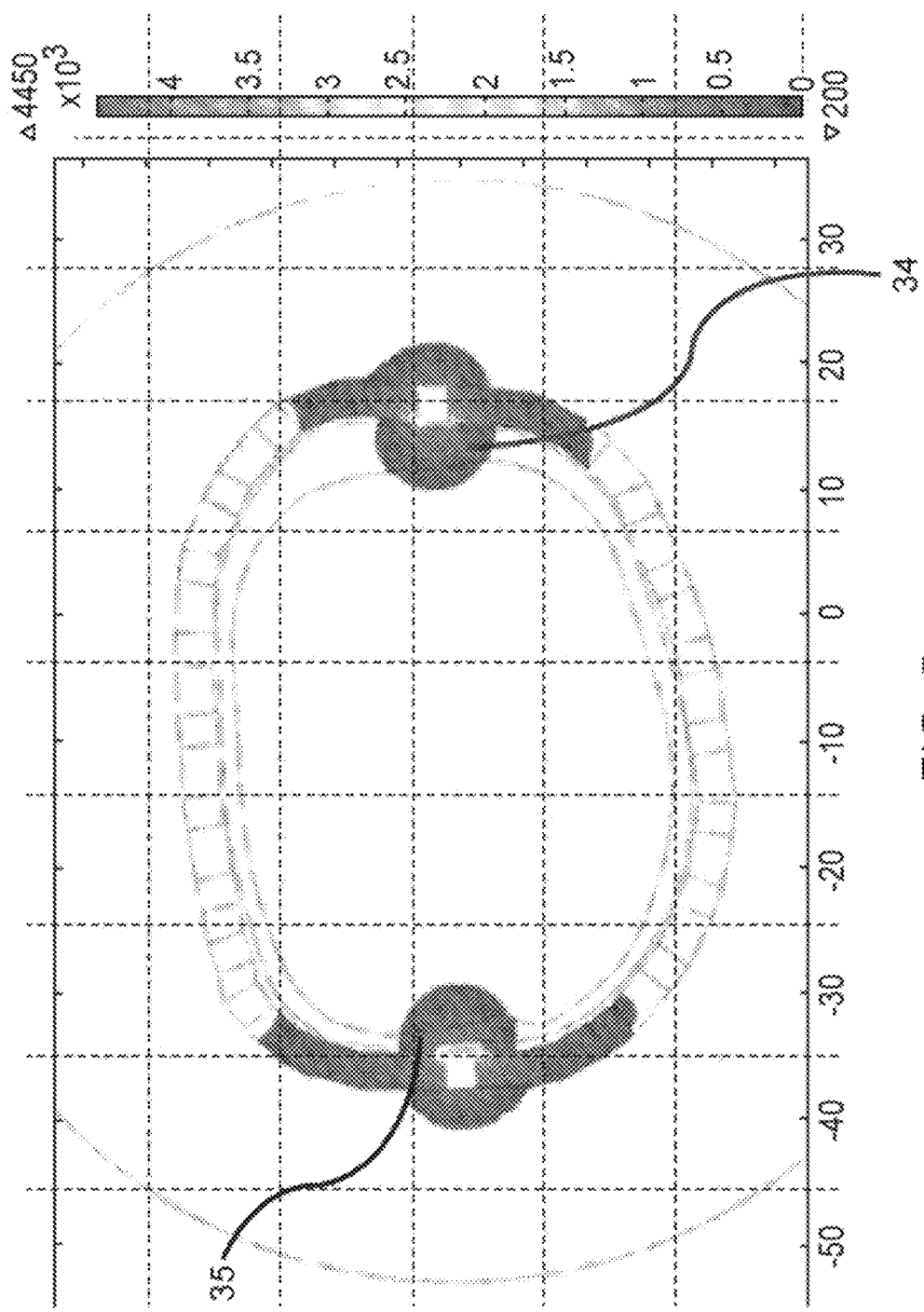
FIG. 5 is a simulation result corresponding to the situation in FIG. 4, in the form of a shaded contour plot of the electric field magnitude in regions where the latter is at least 200 V/cm. with a voltage difference set between two electrodes on opposite sides of the myocardium and all other electrodes replaced by insulation, according to embodiments.

A simulation result in the form of a shaded contour plot of the electric potential is shown in FIG. 4 for the case where a voltage is applied between a single anode electrode 30 and a single cathode electrode 31 on opposite sides of the blood pool region, with all other electrode cells defined to be insulation in terms of electrical properties. In the simulation, a voltage difference of about 1 kV was used between the anode and cathode electrodes. FIG. 5 shows the electric field intensity as a contour plot where regions with an electric field strength of magnitude at least about 200 V/cm (generally needed to cause irreversible electroporation ablation of myocytes) are indicated by the darker shaded areas. It is apparent that these ablated regions, indicated by region 35 around the anode electrode and region 34 around the cathode electrode, are quite localized near the electrodes across which a potential difference is applied.

Figure 6:
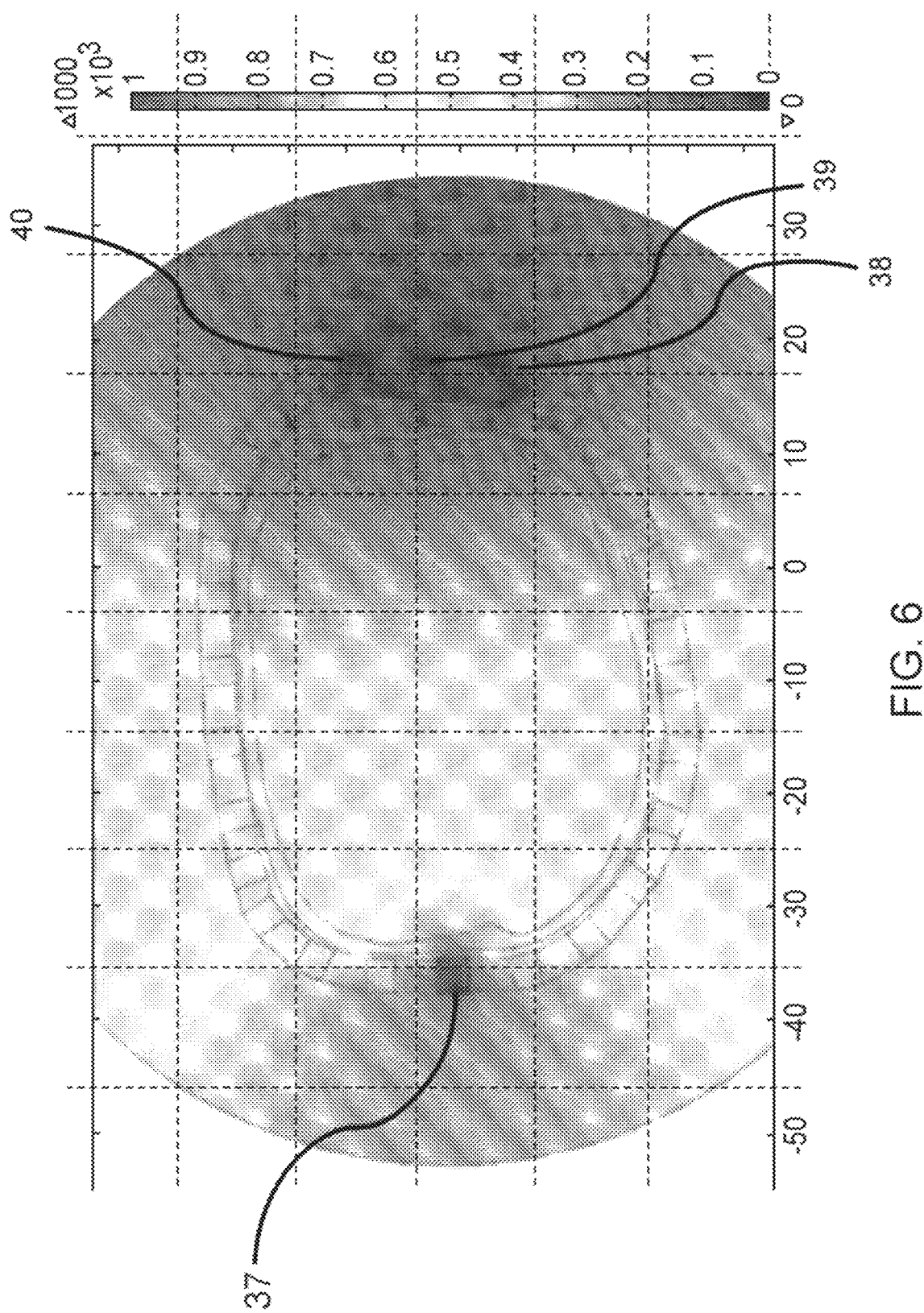
FIG. 6 is a simulation result in the form of a shaded contour plot of the electric potential, with a voltage difference set between one electrode on one side of the myocardium and a set of three contiguous electrodes (separated by insulation between successive pairs) on the opposite side of the myocardium, and all other electrodes replaced by insulation, according to embodiments.
Figure 7:
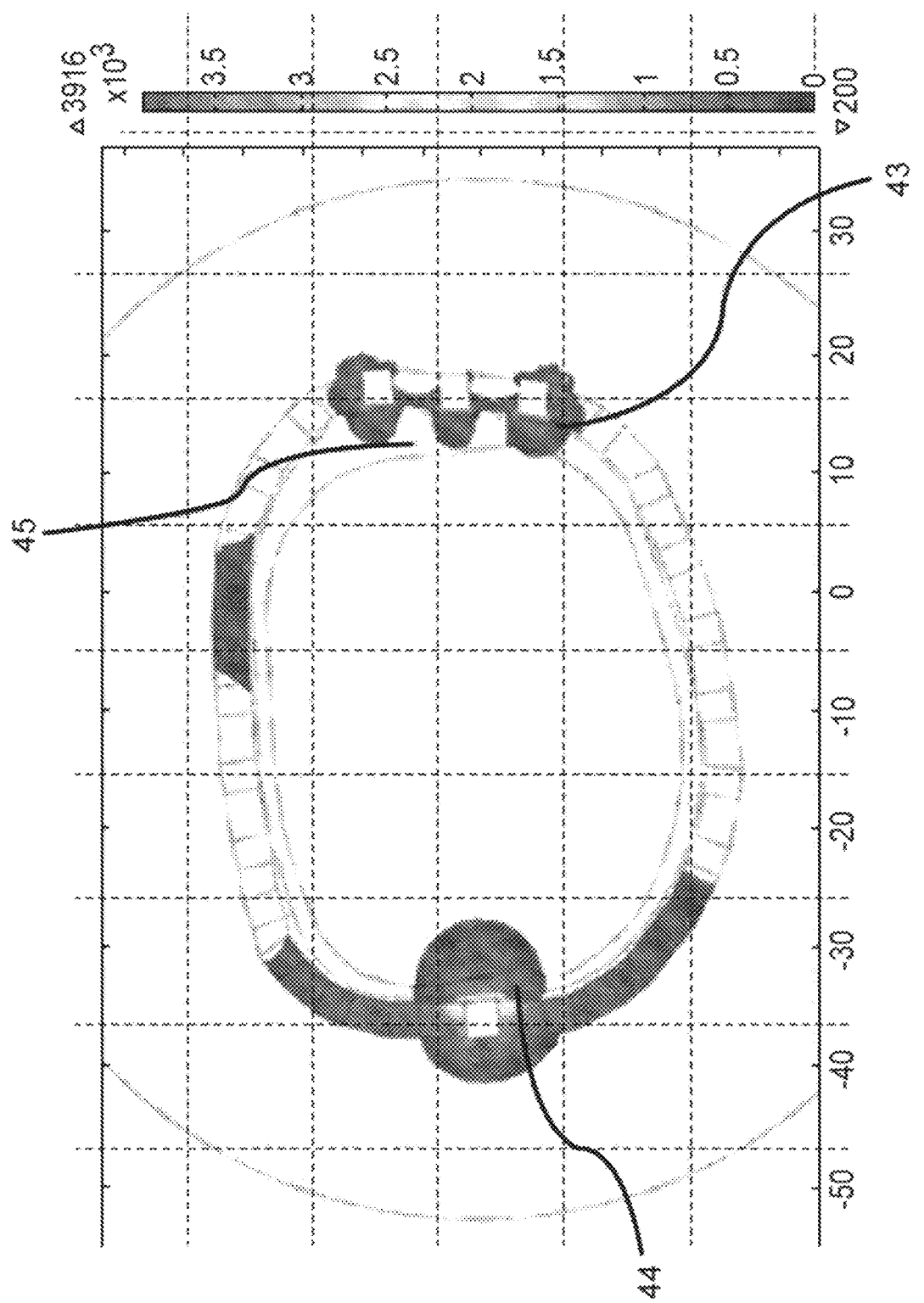
FIG. 7 is a simulation result corresponding to the situation in FIG. 6, in the form of a shaded contour plot of the electric field magnitude in regions where the latter is at least 200 V/cm, with a voltage difference set between one electrode on one side of the myocardium and a set of three contiguous electrodes (separated by insulation between successive pairs) on the opposite side of the myocardium, and all other electrodes replaced by insulation, according to embodiments.

FIG. 6 illustrates a simulation result in the form of a shaded contour plot of the electric potential for the case where a DC voltage is applied between a single anode electrode 37 and a set of three successive cathode electrodes 38, 39 and 40 on opposite sides of the blood pool region, with all other electrode cells defined to be insulation in terms of electrical properties (including cells between electrodes 38 and 39 and between 39 and 40). In the simulation, a voltage difference of about 1 kV was used between the anode and (set of) cathode electrodes. FIG. 7 shows the electric field intensity as a contour plot where regions with an electric field strength of magnitude at least about 200 V/cm (generally needed to cause irreversible electroporation ablation) are indicated by the darker shaded areas. It is apparent that these ablated regions, indicated by region 44 around the anode electrode and region 43 around the set of cathode electrodes, are quite localized near the electrodes across which a potential difference is applied. Furthermore, there are gap regions such as 45 in the myocardium where the electric field intensity is not large enough to generate electroporation. In practice, this would mean that repeated applications of pulsed DC voltage may be needed with repositioning of the catheter shaft(s) and electrodes.

Figure 8:
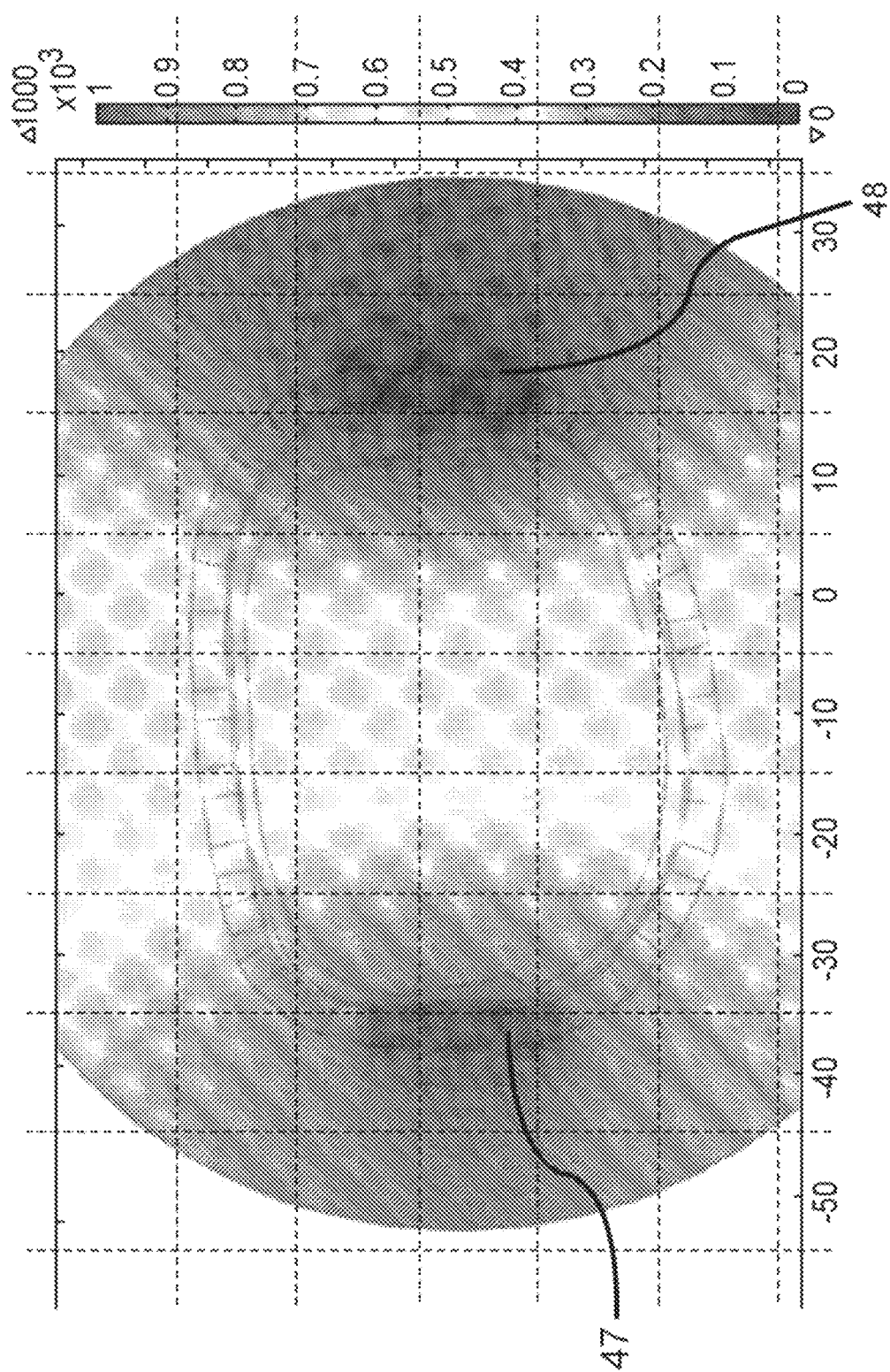
FIG. 8 is a simulation result in the form of a shaded contour plot of the electric potential, with a voltage difference set between a set of five contiguous electrodes on one side of the myocardium and a set of five contiguous electrodes on the opposite side of the myocardium, and all other electrodes replaced by insulation, according to embodiments.
Figure 9:
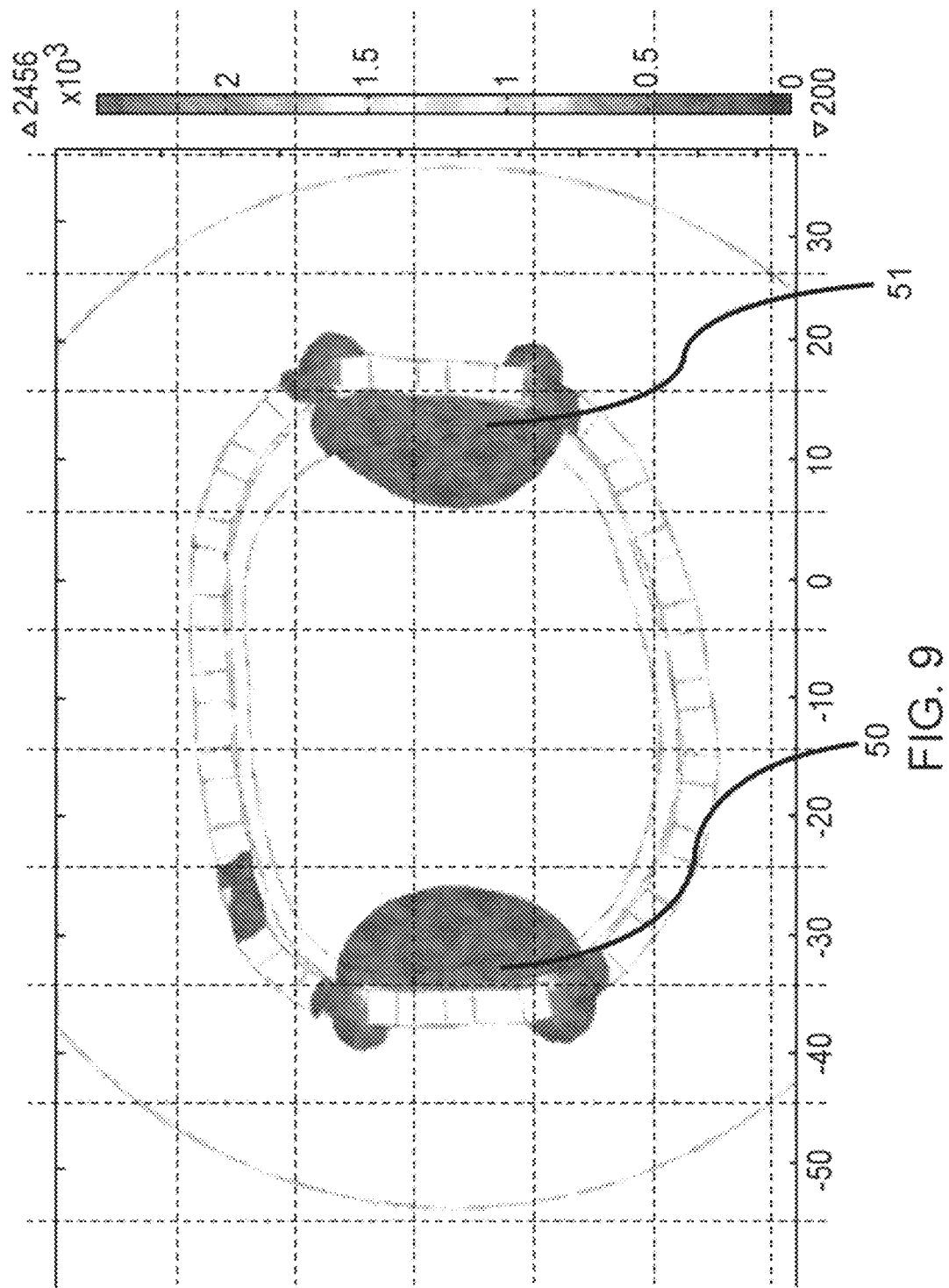
FIG. 9 is a simulation result corresponding to the situation in FIG. 8, in the form of a shaded contour plot of the electric field magnitude in regions where the latter is at least 200 V/cm, with a voltage difference set between a set of three contiguous electrodes (separated by insulation between successive pairs) on one side of the myocardium and a set of three contiguous electrodes (separated by insulation between successive pairs) on the opposite side of the myocardium, and all other electrodes replaced by insulation, according to embodiments.

In FIG. 8, a simulation result is displayed in the form of a shaded contour plot of the electric potential, with a voltage difference set between a set of five contiguous electrodes on one side of the myocardium and a set of five contiguous electrodes on the opposite side of the myocardium, representing respective "long electrodes", and all other electrodes replaced by insulation. In the simulation, a voltage difference of about 1 kV was used between the anode electrode set and the cathode electrode set. FIG. 9 shows the electric field intensity as a contour plot where regions with electric field strength of magnitude at least about 200 V/cm (generally needed to cause irreversible electroporation ablation in myocytes) are indicated by the darker shaded areas. It is apparent that these ablated regions, indicated by region 50 around the anode electrode and region 51 around the set of cathode electrodes, constitute continuous, fully ablated sections of myocardium. Thus, with a set of longer, flexible electrodes as described in the present disclosure, a more rapid and effective delivery of ablation therapy may be obtained as repositioning of the catheter shaft will be minimized. Furthermore, the catheter devices, in some embodiments, with long, flexible electrodes can result in a lower peak value of the electric field. This can minimize or eliminate the possibility of dielectric breakdown or spark generation during high voltage ablation. For instance, while the peak electric field intensity values corresponding to the single cathode and three-cathode situations of FIG. 5 and FIG. 7 are respectively about 4,458 V/cm and about 3,916 V/cm, the peak electric field intensity value that occurs for the case of long, flexible electrodes as in FIG. 8 is about 2,456 V/cm, demonstrating an advantage of the catheter devices of the present disclosure.

Figure 10A:
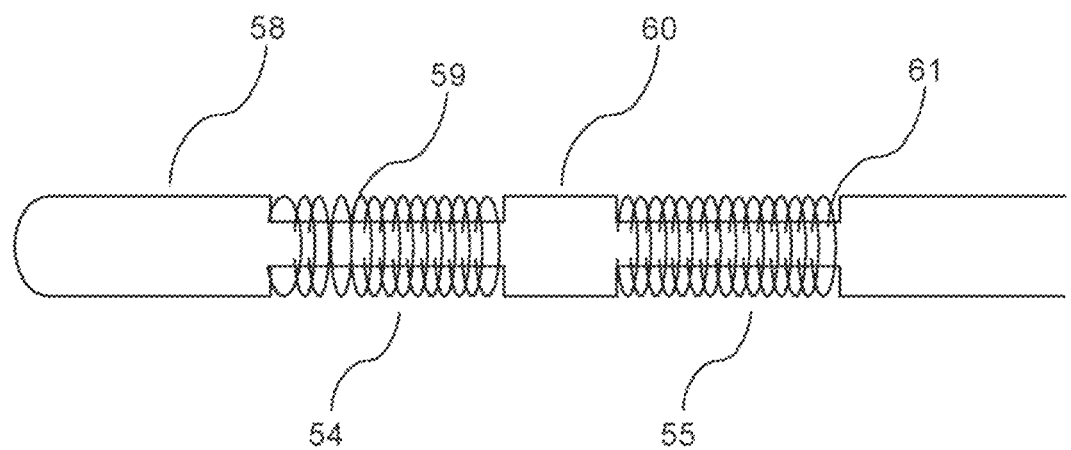
FIG. 10A is an illustration of a catheter with a multiplicity of flexible electrodes disposed along its shaft, each in the form of a coil wound around a stepped structure of the catheter shaft, where the step structure of the shaft and the coil thickness are such that the outer surface of the catheter forms a smooth structure with an even or smooth diameter profile, according to embodiments.

FIG. 10A is a schematic illustration of a catheter with a multiplicity of flexible electrodes disposed along its shaft, with the catheter shaft 58 having a stepped construction consisting of higher profile regions such as 60 and lower profile or "stepped down" regions 59 and 61. Flexible electrodes are present along the stepped down sections 59 and 61 in the form of metallic coils 54 and 55 respectively, such that the overall diameter profile of the catheter shaft is maintained everywhere along its length in a smooth and continuous manner. Thus the thickness of the flexible electrode coils 54 and 55 is such that the sum of the stepped down diameter and twice the coil thickness is equal to the outer diameter of the catheter shaft. The metallic, flexible coiled electrodes could comprise biocompatible metals such as titanium, platinum or platinum alloys. The catheter shaft is made of a flexible polymeric material such as for example Teflon, Nylon or Pebax. In some embodiments, all the electrodes of a catheter have the same polarity, in which case the need for high dielectric strength material separating electrode leads (not shown in FIG. 10A) is not a significant constraint, and the catheter can be relatively small in diameter, for instance being in the range of about 9 French, about 8 French or even about 6 French. Likewise, a higher DC voltage can be applied to the electrodes of the catheter as there is no risk of dielectric breakdown; in some instances, this could enhance the efficacy of irreversible electroporation ablation. The flexible electrode has a length 817 (denoted by L) associated with it, and its diameter 818 corresponds to the catheter diameter (denoted by d). The aspect ratio L/d of each flexible electrode is a geometric characteristic associated with the flexible electrode. In some embodiments, the aspect ratio of at least one of the flexible electrodes on the device is at least 3, and, in some embodiments, at least in the range from 5 to 10. Although FIG. 10A shows two electrodes for purposes of illustration, it should be apparent that the number of flexible electrodes on the catheter can be anywhere from one to fifteen or even greater, depending on the clinical application and convenience of use. In some embodiments, the catheter could have a combination of electrodes such that some electrodes are flexible while others are rigid.

In some embodiments, a flexible electrode may also be constructed in the form of a sequence of thin electrically conducting bands or rings mounted on a flexible catheter shaft, separated by spaces between adjacent rings of the sequence and with the sequence of rings electrically connected together. In this manner, the sequence of rings forms a single electrode, the entire sequence presenting an isopotential surface across which an electrical current can flow to tissue adjacent to the electrode when the electrode is suitably electrically polarized. The electrical connection between the individual rings of the sequence can be made by several means, such as, for example, attaching a single electrical lead to the inner surface of each ring with one or more spot welds or laser welding, or by crimping each electrode in place over a portion of an exposed electrical lead that runs on the outer surface of the catheter shaft, and so on.

Figure 10B:
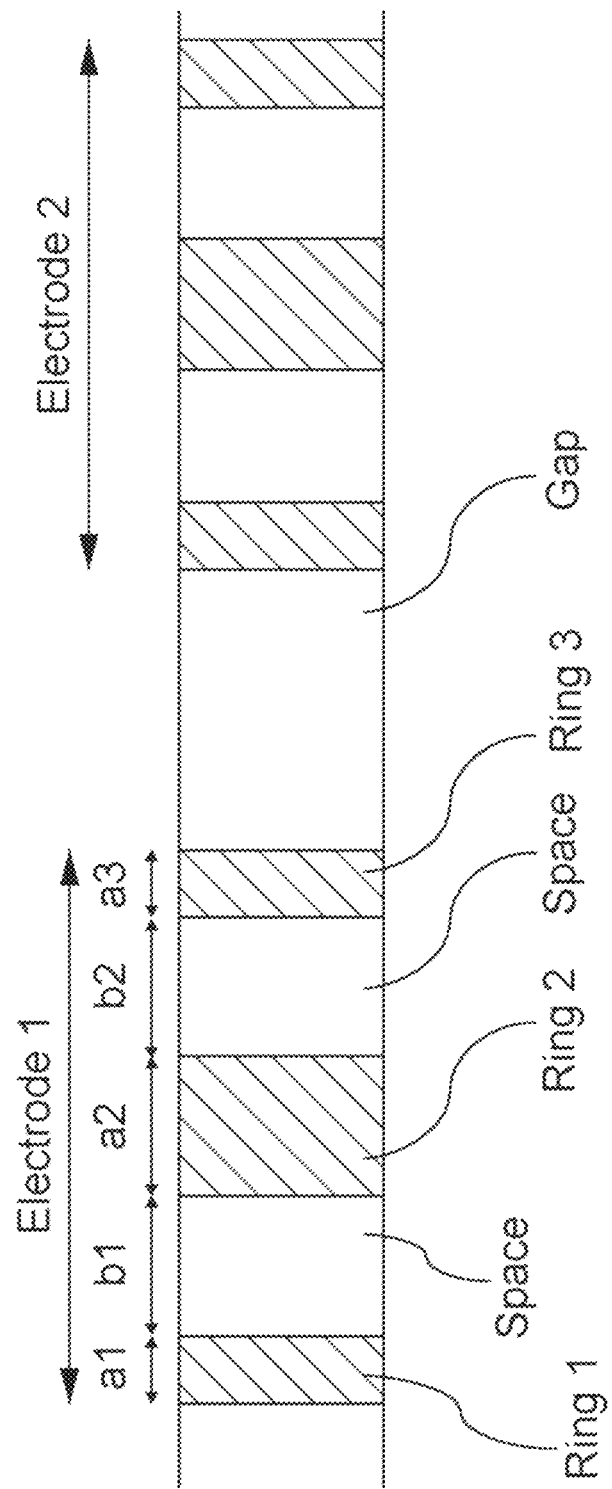
FIG. 10B is an illustration of construction of two flexible electrodes, according to embodiments.

The construction of such a flexible electrode is illustrated in the example in FIG. 10B, where two such electrodes are shown disposed along a length of flexible catheter shaft. Each electrode in the figure includes 3 electrically conducting rings (Rings 1, 2, 3) separated by spaces. FIG. 10B shows 3 rings of widths $a_1$, $a_2$ and $a_3$ with rings 1 and 2 separated by a space of width $b_1$ and rings 2 and 3 separated by a space of width $b_2$. Since only the flexible catheter shaft is present in the spaces, even though the individual rings may be rigid (for example, the rings can be metallic), the electrode itself is effectively flexible. The adjacent electrodes are separated by a gap. In this manner, the catheter itself can also bend in very flexible fashion. The width of each ring of a flexible electrode can lie in the range between about 0.5 mm and about 6 mm, or in the range between about 1 mm and about 4 mm, including all values and sub ranges in between. The spaces between adjacent rings can lie in the range between about 1 mm and about 4 mm, including all values and sub ranges in between. Further, the gaps or separation between adjacent distinct electrodes can lie in the range between about 2 mm and about 12 mm, including all values and sub ranges in between.

In the example shown in FIG. 10B, the central or second ring of the flexible electrode is wider than the end rings (1 and 3). While this example shows a flexible electrode comprising 3 conducting rings, more general constructions with a larger or smaller multiplicity of conducting rings can be built by one skilled in the art following the disclosure herein. Likewise, the separations between adjacent rings can be varied sequentially, as can the width of each individual ring in the sequence. The above example is provided for non-limiting illustrative purposes only.

For epicardial use as disclosed in the present application, it is useful to have a catheter with a certain amount of flexibility. One characterization of flexibility can be made in terms of a radius of curvature. In some embodiments, the flexible electrodes are constructed and disposed along the catheter shaft such that about a 2 cm radius of curvature of the shaft is achieved with a minimal amount of applied force or torque. In some embodiments, a bending moment of about $5 \times 10^{-3}$ N-m applied over an approximately 6 cm length of catheter can result in a bend or end-to-end deflection in the catheter of about 180-degrees or larger.

The rings of each flexible electrode can be of metallic composition including, but not limited to, stainless steel, silver, gold, any suitable material comprising a significant proportion of platinum such as platinum-iridium alloy, combinations thereof, and/or the like.

Figure 11:
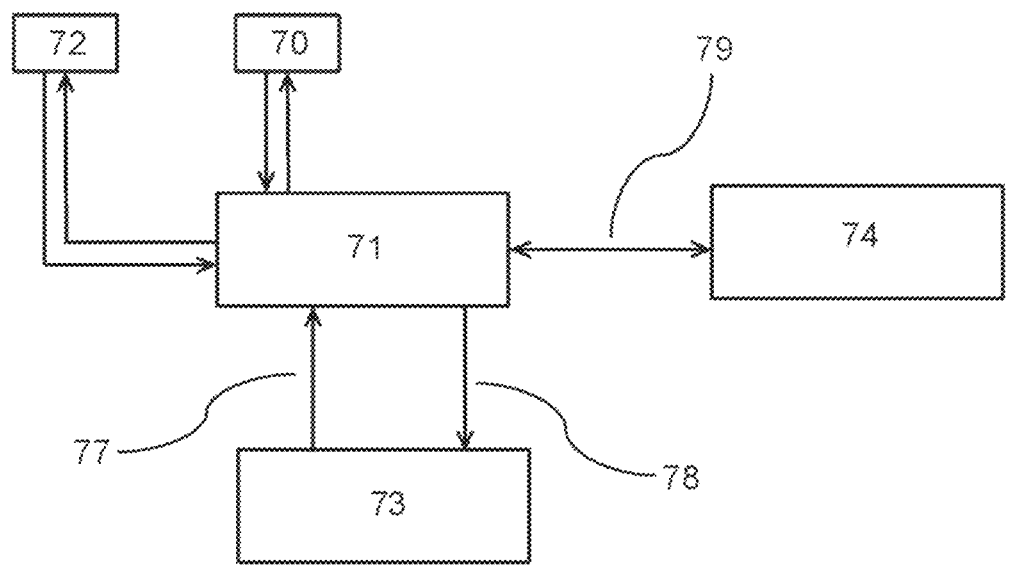
FIG. 11 is a schematic illustration of an irreversible electroporation system that includes a voltage/signal generator, a controller capable of being configured to apply voltages to selected subsets of electrodes with independent subset selections for anode electrodes on one medical device and cathode electrodes on a second medical device and that is connected to a computer, and two or more medical devices connected to the controller, according to embodiments.

A schematic diagram of the electroporation system, according to some embodiments, is shown in FIG. 11. A voltage/signal generator 73 is driven by a controller unit 71 that interfaces with a computer device 74 by means of a two-way communication link 79. The controller interface can act as a multiplexer unit and perform channel selection and routing functions for applying voltages to appropriate electrodes that have been selected by a user or by the computer 74. The controller can apply the voltages via a multiplicity of leads to a first catheter device 72, as well as a second catheter device 70. Active electrodes can be selected on a first catheter device 72 with one polarity, and likewise active electrodes can be selected on a second catheter device 70 with the opposite polarity.

Some leads from the controller 71 could also carry pacing signals to drive pacing of the heart through a separate pacing device (not shown). The catheter devices can also send back information such as ECG recordings or data from other sensors back to the controller 71, possibly on separate leads. While the voltage generator 73 sends a voltage to the controller 71 through leads 77, the voltage generator is driven by control and timing inputs 78 from the controller unit 71.

Figure 12:
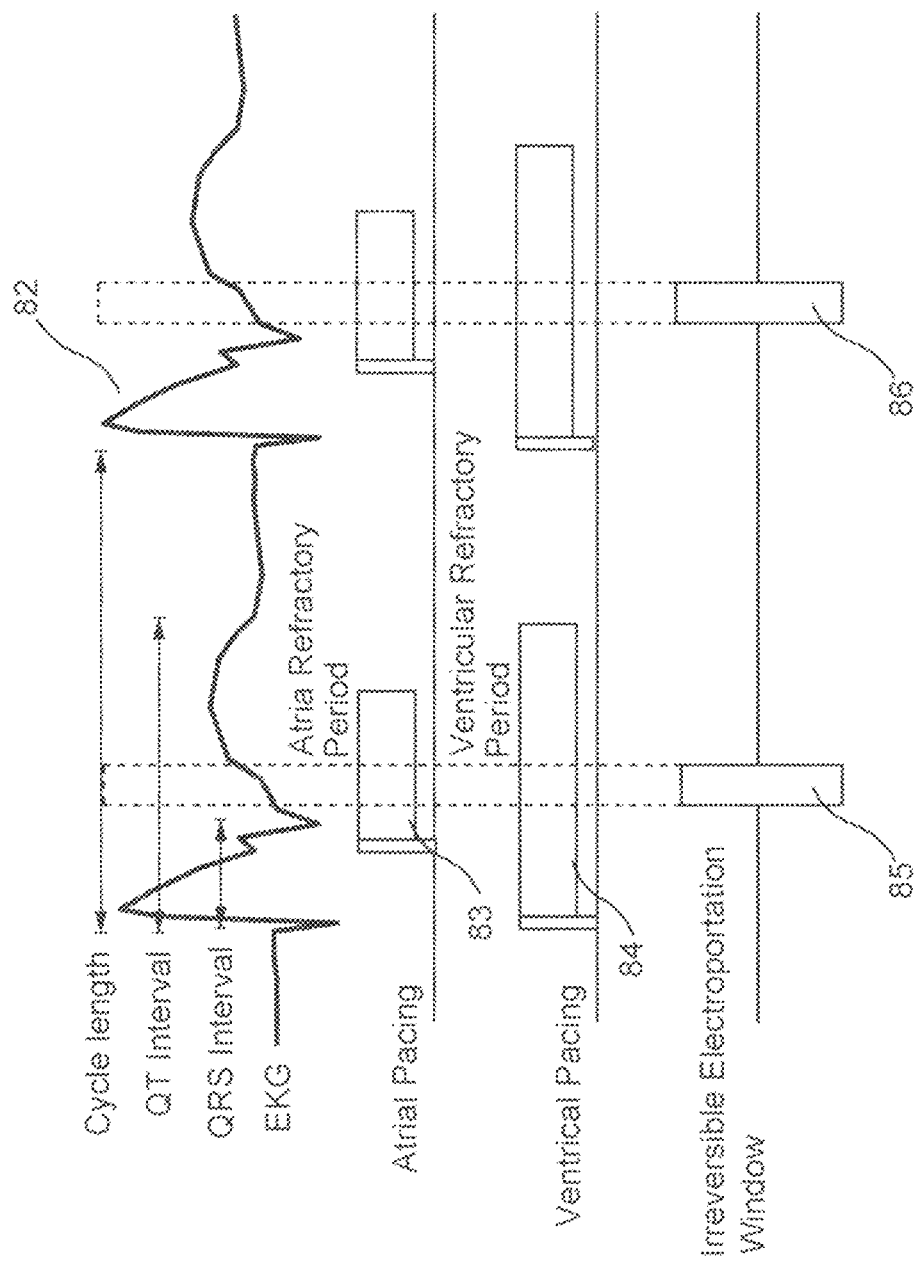
FIG. 12 is an illustration of an ECG waveform showing the refractory periods during atrial and ventricular pacing during which a time window for irreversible electroporation ablation can be chosen, according to embodiments.

As shown in FIG. 12, given atrial or ventricular pacing inputs to the heart, the resulting ECG waveform 82 has appropriate respective refractory time intervals 83 and 84 respectively, during which there are suitable time windows for application of irreversible electroporation as indicated by 85 and 86. The application of cardiac pacing results in a periodic, well-controlled sequence of electroporation time windows. Typically, this time window is of the order of hundreds of microseconds to about a millisecond or more. During this window, multiple voltage pulses can be applied to ensure that sufficient tissue ablation has occurred. The user can repeat the delivery of irreversible electroporation over several successive cardiac cycles for further confidence.

In one embodiment, the ablation controller and signal generator can be mounted on a rolling trolley, and the user can control the device using a touchscreen interface that is in the sterile field. The touchscreen can be for example an LCD touchscreen in a plastic housing mountable to a standard medical rail or post and can be used to select the electrodes for ablation and to ready the device to fire. The interface can for example be covered with a clear sterile plastic drape. The operator can select the number of electrodes involved in an automated sequence. The touch screen graphically shows the catheters that are attached to the controller. In one embodiment the operator can select electrodes from the touchscreen with appropriate graphical buttons. The operator can also select the pacing stimulus protocol (either internally generated or externally triggered) from the interface. Once pacing is enabled, and the ablation sequence is selected, the operator can initiate or verify pacing. Once the operator verifies that the heart is being paced, the ablation sequence can be initiated by holding down a hand-held trigger button that is in the sterile field. The hand-held trigger button can be illuminated red to indicate that the device is "armed" and ready to ablate. The trigger button can be compatible for use in a sterile field and when attached to the controller can be illuminated a different color, for example white. When the device is firing, the trigger button flashes in sequence with the pulse delivery in a specific color such as red. The waveform of each delivered pulse is displayed on the touchscreen interface. A graphic representation of the pre and post impedance between electrodes involved in the sequence can also be shown on the interface, and this data can be exported for file storage.

In one embodiment, impedance readings can be generated based on voltage and current recordings across anode-cathode pairs or sets of electrodes (anodes and cathodes respectively being on distinct catheters), and an appropriate set of electrodes that are best suited for ablation delivery in a given region can be selected based on the impedance map or measurements, either manually by a user or automatically by the system. For example, if the impedance of the tissue between an anode/cathode combination of electrodes is a relatively low value (for example, less than 25 Ohms), at a given voltage the said combination would result in relatively large currents in the tissue and power dissipation in tissue; this electrode combination would then be ruled out for ablation due to safety considerations, and alternate electrode combinations could be sought by the user. In some embodiments, a pre-determined range of impedance values, for example 30 Ohms to 300 Ohms, could be used as an allowed impedance range within which it is deemed safe to ablate.

The waveforms for the various electrodes can be displayed and recorded on the case monitor and simultaneously outputted to a standard connection for any electrophysiology (EP) data acquisition system. With the high voltages involved with the device, the outputs to the EP data acquisition system needs to be protected from voltage and/or current surges. The waveforms acquired internally can be used to autonomously calculate impedances between each electrode pair. The waveform amplitude, period, duty cycle, and delay can all be modified, for example via a suitable Ethernet connection. Pacing for the heart is controlled by the device and outputted to the pacing leads and a protected pacing circuit output for monitoring by a lab.

In some embodiments, the system (generator and controller) can deliver rectangular-wave pulses with a peak maximum voltage of about 5 kV into a load with an impedance in the range of about 30 Ohm to about 3,000 Ohm for a maximum duration of about 200 µs, with a maximum duration of about 100 µs, in some embodiments. Pulses can be delivered in a multiplexed and synchronized manner to a multi-electrode catheter inside the body with a duty cycle of up to 50% (for short bursts). The pulses can generally be delivered in bursts, such as for example a sequence of between 2 and 10 pulses interrupted by pauses of between about 1 ms and about 1,000 ms. The multiplexer controller is capable of running an automated sequence to deliver the impulses/impulse trains (from the voltage signal/impulse generator) to the tissue target within the body. The controller system is capable of switching between subsets of electrodes located on the single-use catheters. Further, the controller can measure voltage and current and tabulate impedances of the tissue in each electrode configuration (for display, planning, and internal diagnostic analysis). It can also generate two channels of cardiac pacing stimulus output, and is capable of synchronizing impulse delivery with the internally generated cardiac pacing and/or an external trigger signal. In one embodiment, it can provide sensing output/connection for access to bio potentials emanating from each electrode connected to the system (with connectivity characteristics being compatible with standard electrophysiological laboratory data acquisition equipment).

In some embodiments, the controller can automatically "recognize" each of the two single-use disposable catheters when it is connected to the controller output (prompting internal diagnostics and user interface configuration options). The controller can have at least two unique output connector ports to accommodate up to at least two catheters at once. The controller device can function as long as at least two recognized catheters are attached to it. In some embodiments, the controller can have several sequence configurations that provide the operator with at least some variety of programming options. In one configuration, the controller can switch electrode configurations of a bipolar set of electrodes (cathodes and anodes respectively on distinct catheters) sequentially, for instance in a clockwise manner (for example, starting at a given step, in the next step of the algorithm, the next cathode electrode on one catheter and the next anode electrode on the other catheter are automatically selected, timed to the synchronizing trigger), with the two catheters and their electrodes arranged in a quasi-circumference around the target. Thus in a first sequence configuration, pulsed voltage delivery occurs as the automated sequencing of the controller switches "on" and "off" between different electrodes surrounding the tissue target. In a second sequence configuration, the impulses are delivered to user-selected electrode subsets of catheters that are connected to the device. The user can also configure the controller to deliver up to 2 channels of pacing stimulus to electrodes connected to the device output. The user can control the application of voltage with a single handheld switch. A sterile catheter or catheters can be connected to the voltage output of the generator via a connector cable that can be delivered to the sterile field. In one embodiment, the user activates the device with a touch screen interface (that can be protected with a single-use sterile transparent disposable cover commonly available in the catheter lab setting). The generator can remain in a standby mode until the user is ready to apply pulses at which point the user/assistant can put the generator into a ready mode via the touchscreen interface. Subsequently the user can select the sequence, the active electrodes, and the cardiac pacing parameters.

Once the catheters have been advanced to or around the cardiac target, the user can initiate electrically pacing the heart (using a pacing stimulus generated by the ablation controller or an external source synchronized to the ablation system). The operator verifies that the heart is being paced and uses the hand-held trigger button to apply the synchronized bursts of high voltage pulses. The system can continue delivering the burst pulse train with each cardiac cycle as long as the operator is holding down a suitable "fire" button or switch. During the application of the pulses, the generator output is synchronized with the heart rhythm so that short bursts are delivered at a pre-specified interval from the paced stimulus. When the train of pulses is complete, the pacing continues until the operator discontinues pacing.

Figure 13:
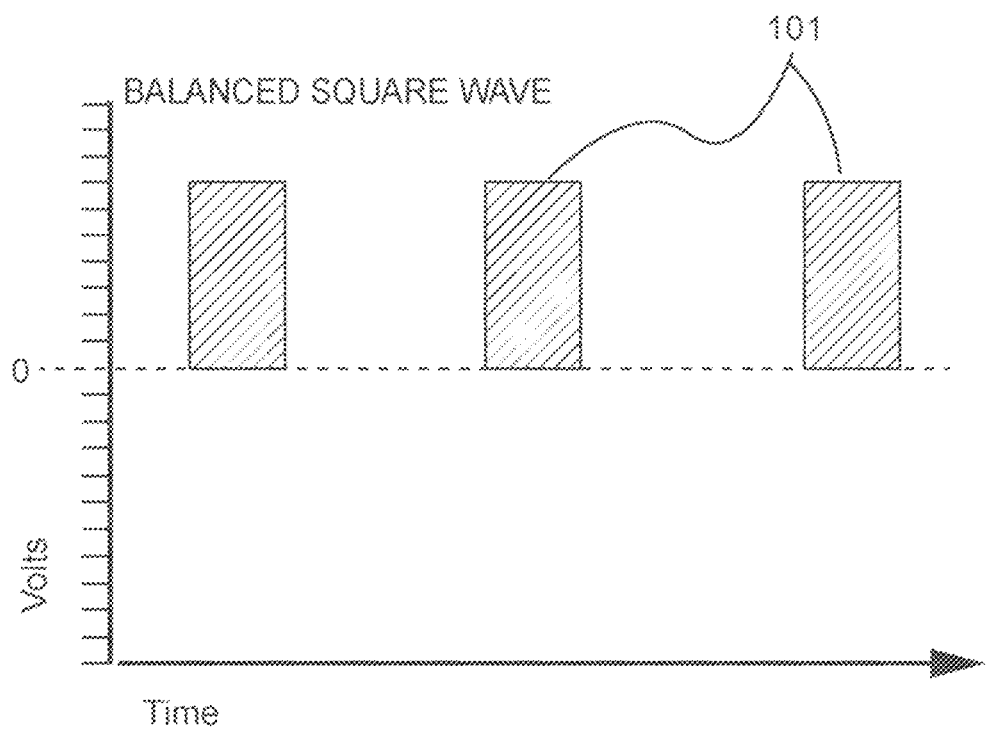
FIG. 13 is a schematic illustration of a waveform generated by the irreversible electroporation system according to embodiments, showing a balanced square wave.
Figure 14:
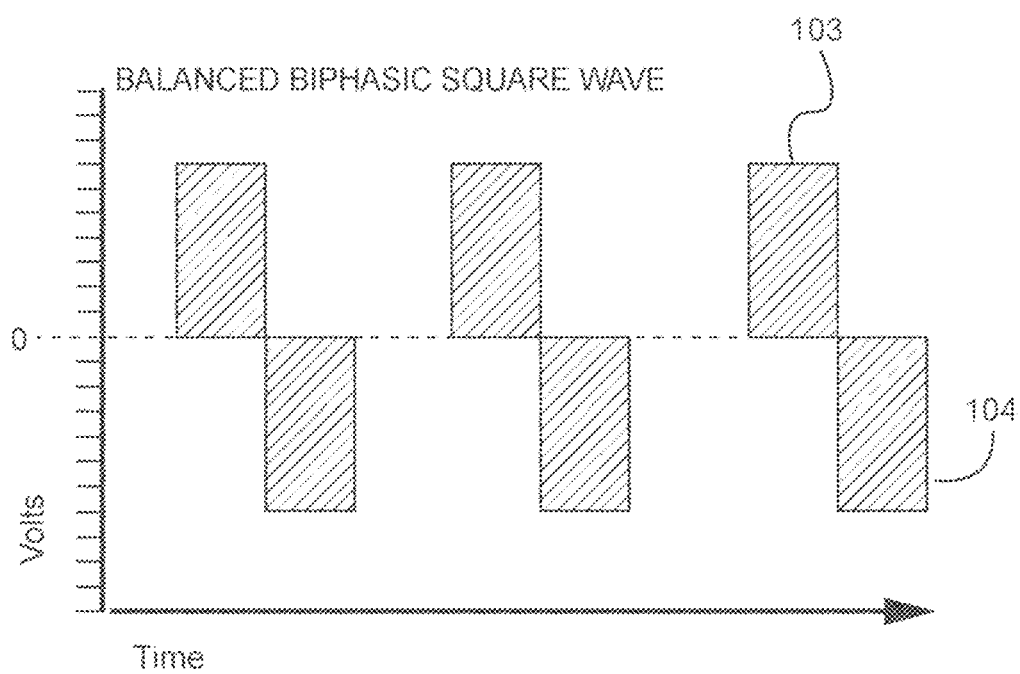
FIG. 14 is a schematic illustration of a waveform generated by the irreversible electroporation system according to embodiments, showing a balanced biphasic square wave.

The controller and generator can output waveforms that can be selected to generate a sequence of voltage pulses in either monophasic or biphasic forms and with either constant or progressively changing amplitudes. FIG. 13 shows a rectangular wave pulse train where the pulses 101 have a uniform height or maximum voltage. FIG. 14 shows an example of a balanced biphasic rectangular pulse train, where each positive voltage pulse such as 103 is immediately followed by a negative voltage pulse such as 104 of equal amplitude and opposite sign. While in this example the biphasic pulses are balanced with equal amplitudes of the positive and negative voltages, in other embodiments an unbalanced biphasic waveform could also be used as may be convenient for a given application.

Figure 15:
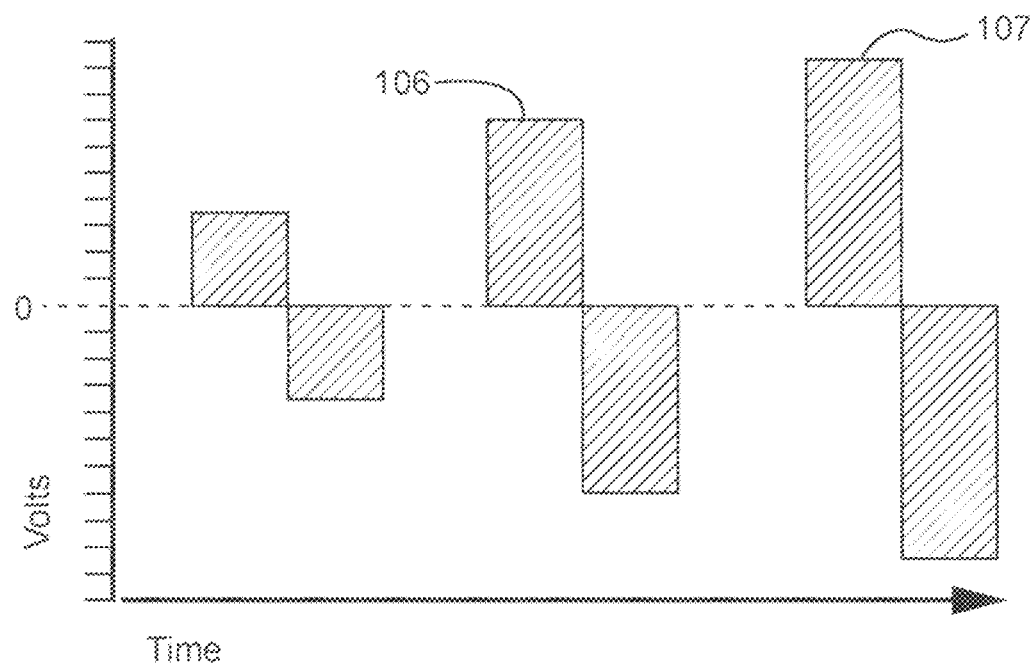
FIG. 15 is a schematic illustration of a waveform generated by the irreversible electroporation system according to embodiments, showing a progressive balanced biphasic square wave.

Yet another example of a waveform or pulse shape that can be generated by the system is illustrated in FIG. 15, which shows a progressive balanced rectangular pulse train, where each distinct biphasic pulse has balanced or equal-amplitude positive and negative voltages, but each pulse such as 107 is larger in amplitude than its immediate predecessor 106. Other variations such as a progressive unbalanced rectangular pulse train, or indeed a wide variety of other variations of pulse amplitude with respect to time can be conceived and implemented by those skilled in the art based on the teachings herein.

The time duration of each irreversible electroporation rectangular voltage pulse could lie in the range from about 1 nanosecond to about 10 milliseconds, with the range about 10 microseconds to about 1 millisecond in some embodiments, and the range about 50 microseconds to about 300 microseconds in some embodiments, including all values and sub ranges in between. The time interval between successive pulses of a pulse train could be in the range of about 10 microseconds to about 1 millisecond, with the range about 50 microseconds to about 300 microseconds in some embodiments. The number of pulses applied in a single pulse train (with delays between individual pulses lying in the ranges just mentioned) can range from 1 to 100, with the range 1 to 10 in some embodiments.

As described in the foregoing, a pulse train can be driven by a user-controlled switch or button or, in some embodiments, mounted on a hand-held joystick-like device. In one mode of operation a pulse train can be generated for every push of such a control button, while in another mode of operation pulse trains can be generated repeatedly during the refractory periods of a set of successive cardiac cycles, for as long as the user-controlled switch or button is engaged by the user.

All of these parameters can be determined by the design of the signal generator, and in various embodiments could also be determined by user control as may be convenient for a given clinical application. The specific examples and descriptions herein are exemplary in nature and variations can be developed by those skilled in the art based on the material taught herein.

Figure 16:
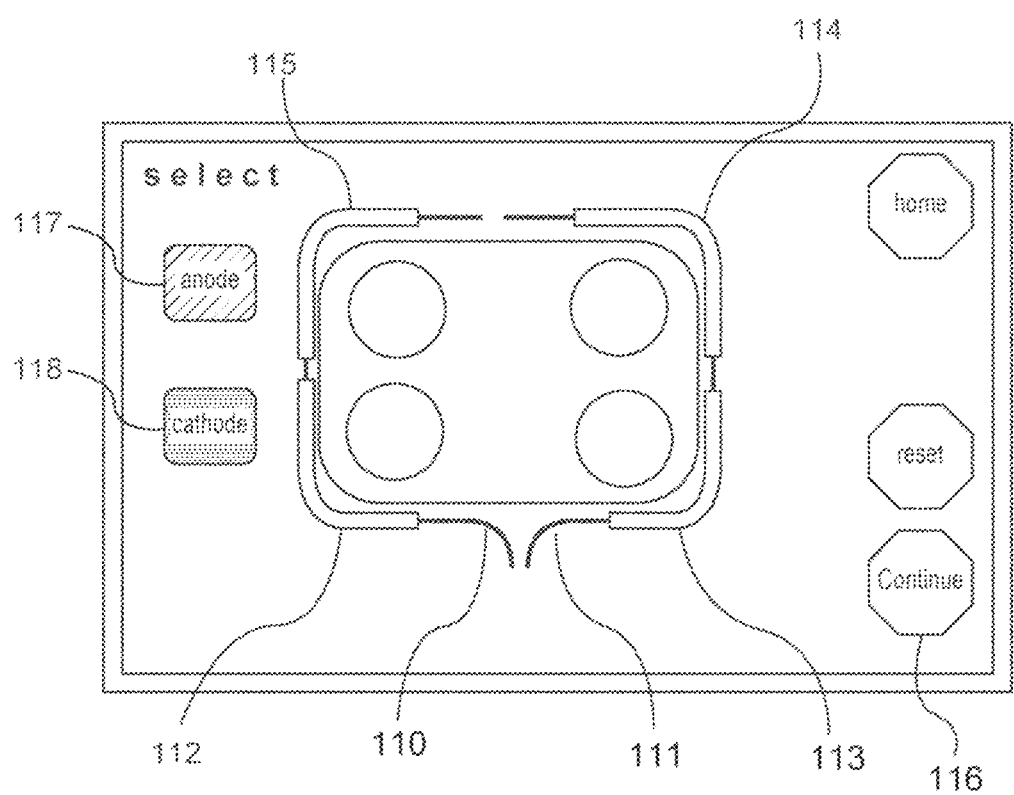
FIG. 16 is a schematic illustration of a user interface according to embodiments, showing electrodes on two catheters, and buttons for selection or marking of anode electrode subsets and cathode electrode subsets.

FIG. 16 shows a portion of a user interface of the electroporation system for selection (with graphical buttons 117 and 118) of anode and cathode electrodes, with two catheters connected to the system. The proximal leads of the two catheters are schematically indicated by 110 and 111, which each have two flexible electrodes, respectively 112, 115 and 113, 114. The buttons 117 and 118 can enable the selection of appropriate electrodes on the catheters as respectively anode or cathode with a "Continue" button 706. Once the selection is made, the appropriate electrodes are colored differently to indicate anode or cathode electrodes as shown marked respectively as anode electrode 115 and cathode electrode 113 on the two catheters in FIG. 17.

Figure 18:
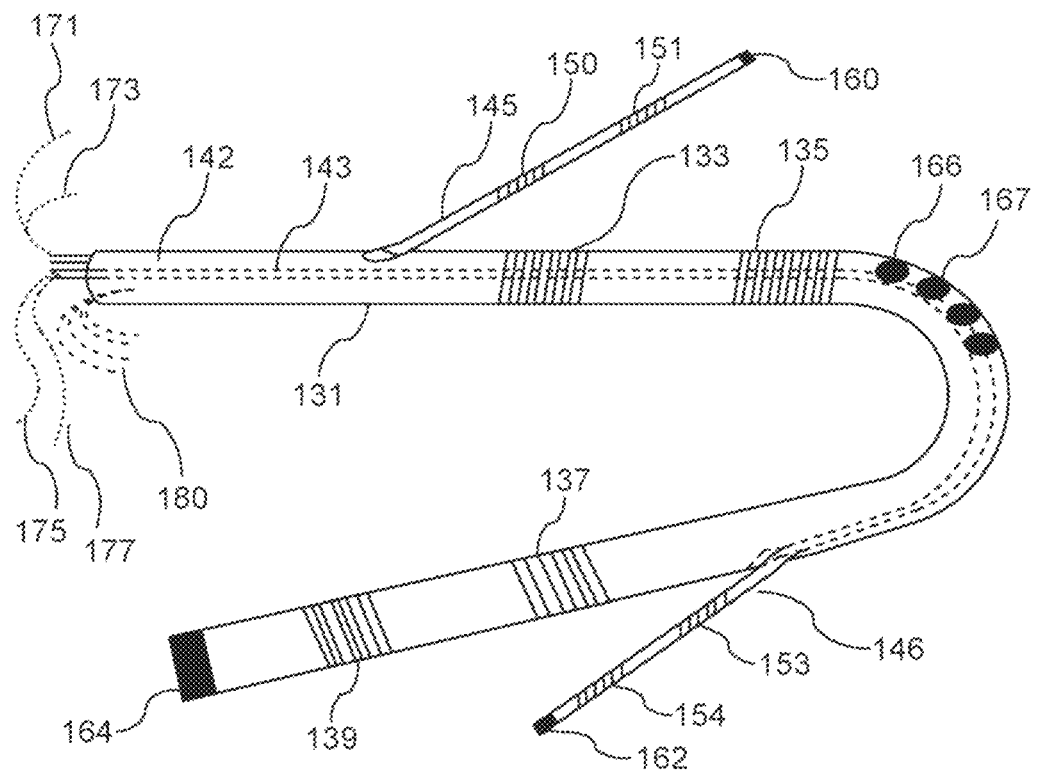
FIG. 18 illustrates a first or primary catheter with a multiplicity of flexible electrodes disposed along its shaft with an electrical lead attached to the inner surface of each electrode, and endowed with multiple lumens through which secondary catheters or microcatheters are passed to emerge from a lateral surface of the primary catheter, each secondary catheter also having a multiplicity of flexible electrodes disposed along its shaft, according to embodiments.

FIG. 18 shows another embodiment of device of the present disclosure, where a first or primary catheter with a multiplicity of flexible electrodes disposed along its shaft (with an electrical lead attached to the inner surface of each electrode) includes multiple lumens through which secondary catheters or microcatheters can be passed to emerge from a lateral surface of the primary catheter, each secondary catheter also having a multiplicity of flexible electrodes disposed along its shaft. In the illustration, the primary catheter device 131 has flexible electrodes 133, 135, 137 and 139 disposed along the length of its shaft, and the device 131 has lumens 142 and 143 through which secondary catheter devices 145 and 146 are passed. The secondary catheters pass through the lumens and emerge from a lateral portion of the primary catheter, in some embodiments on approximately opposite lateral sides of the primary catheter 131. The secondary catheters 145 and 146 themselves have a multiplicity of flexible electrodes disposed along their lengths, shown in FIG. 18 as electrodes 150 and 151 on secondary catheter 145 and as electrodes 153 and 154 on secondary catheter 146, respectively. Electrical leads 180 connect to the electrodes 133, 135, 137 and 139 of the primary catheter for delivery of high voltage pulsed signals. In one embodiment the same leads 180 can also serve to record ECG signals. Likewise electrical leads 171 and 173 connect to electrodes 150 and 151 on secondary catheter 145, while electrical leads 175 and 177 connect to electrodes 153 and 154 on secondary catheter 146. The distal region of the primary catheter 131 comprises a magnetic member 164, and magnetic members such as 166 or 167 are also present within the primary catheter's shaft at an approximately mid-length position. The distal regions of the secondary catheters 145 and 146 also comprise magnetic members 160 and 162 respectively. In some embodiments, the magnetic member 164 comprises at least one permanent magnet, while the magnetic members 160 and 162 comprise magnetizable material such as a ferromagnetic material, while the magnetic members 166 and 167 can be either permanent magnets or electromagnets activated by an electrical current, with their magnetic poles oriented laterally with respect to the catheter shaft. Further the primary catheter can have a through lumen (not shown in FIG. 18) for introducing the catheter over a guidewire.

Figure 19:
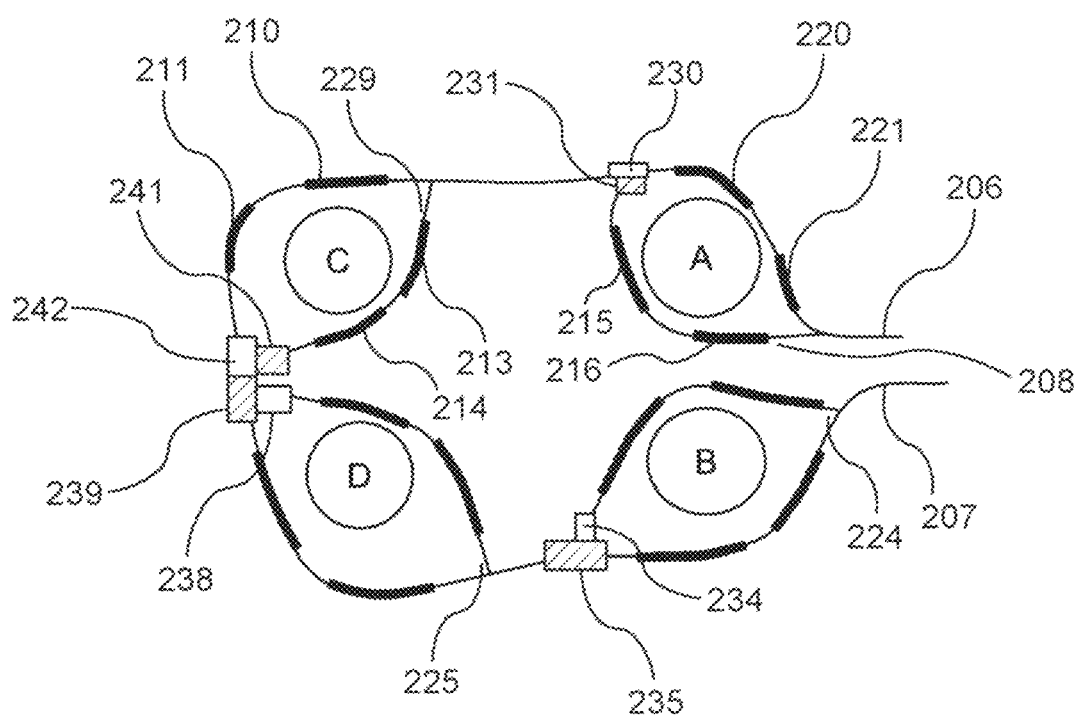
FIG. 19 provides a schematic illustration of two primary catheters that together encircle a set of four pulmonary veins, with two secondary catheters emerging from each primary catheter so as to conjunctively wrap a set of electrodes around each individual pulmonary vein, according to embodiments.

In use, as FIG. 19 illustrates, two primary catheters are introduced epicardially via a subxiphoid approach as described for example in PCT Patent Application No. WO2014025394, where a puncturing apparatus using a subxiphoid pericardial access location and a guidewire-based delivery method to accomplish the placement of a multi-electrode catheter around the pulmonary veins was described in detail. The two primary catheters jointly encircle a set of four pulmonary veins, with two secondary catheters emerging from each primary catheter so as to conjunctively wrap a set of electrodes around each individual pulmonary vein. Four pulmonary veins marked A, B, C and D are shown in FIG. 19. Primary catheter 206 wraps around one side (representing an outer contour) of pulmonary veins marked A and C in FIG. 19, while primary catheter 207 wraps around one side (representing an outer contour) of pulmonary veins marked B and D in FIG. 19. Secondary catheter 208 branches out from a proximal portion of primary catheter 206, wraps around the inner side of pulmonary vein A and magnetically attaches to the mid-portion of primary catheter 206, with a distal magnetic member 231 on secondary catheter 208 attaching to a mid-portion magnetic member 230 on primary catheter 206. Thus secondary catheter electrodes 215 and 216 and primary catheter electrodes 220 and 221 collectively are wrapped in a closed contour around pulmonary vein A. Secondary catheter 229 branches out from a middle portion of primary catheter 206, wraps around the inner side of pulmonary vein C and magnetically attaches to the distal portion of primary catheter 206, with a distal magnetic member 241 on secondary catheter 229 attaching to a distal magnetic member 242 on primary catheter 206. Thus secondary catheter electrodes 213 and 214 and primary catheter electrodes 210 and 211 collectively are wrapped in a closed contour around pulmonary vein C. The distal portion of primary catheter 206 also magnetically attaches to the distal portion of primary catheter 207. Secondary catheters 224 and 225 branch out from primary catheter 207 and wrap around pulmonary veins B and D, with a distal magnetic member 234 on secondary catheter 224 attaching to a mid-portion magnetic member 235 on primary catheter 207 and a distal magnetic member 238 on secondary catheter 225 attaching to a distal magnetic member 239 on primary catheter 207, respectively. In this manner, each pulmonary vein is wrapped by a set of flexible electrodes for effective electroporation voltage delivery.

Figure 20:
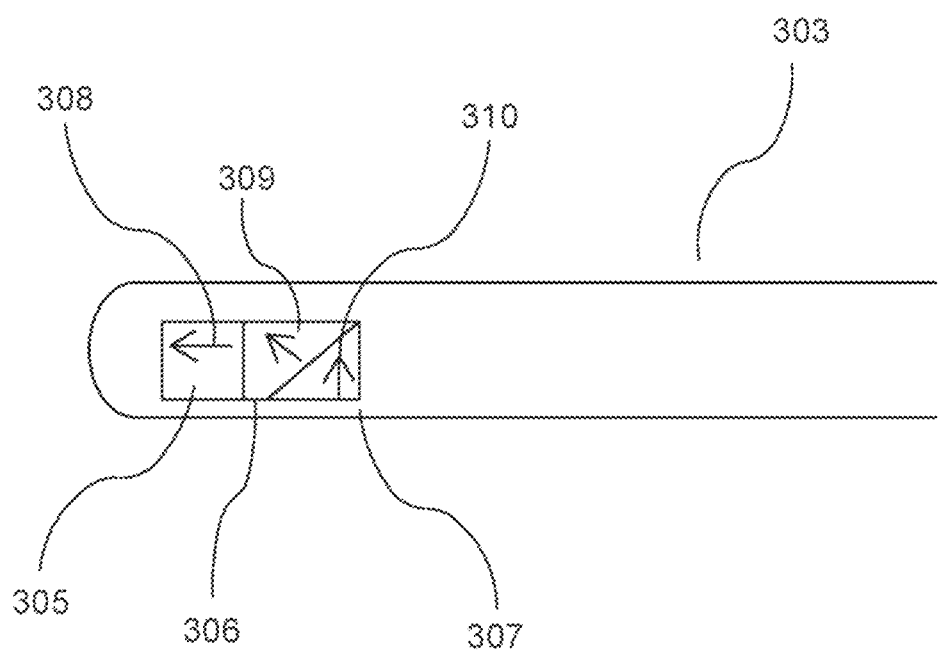
FIG. 20 is an illustration of a catheter with a magnet assembly in its distal portion, such that a first effective pole of the magnet assembly is oriented longitudinally and a second effective pole of the magnet assembly oriented laterally, according to embodiments.

An example of a magnetic member configuration for the distal magnetic member 164 of the primary catheter device in FIG. 18 (or 239 or 242 in FIG. 19) is provided in FIG. 20. The latter figure illustrates a catheter with a magnet assembly in its distal portion, such that a first effective pole of the magnet assembly is oriented longitudinally and a second effective pole of the magnet assembly oriented laterally. As shown, the catheter 303 comprises an assembly of magnetized material in its distal portion comprising magnetic elements 305, 306 and 307 with respective magnetization orientations indicated by arrows 308, 309 and 310. The assembly comprising the magnetic elements 305, 306 and 307 effectively forms a magnetic member with a longitudinally oriented magnetic pole (denoted by arrow 308) and a laterally oriented magnetic pole (denoted by arrow 310). If a second primary catheter has a similar assembly of magnetic elements in its distal portion with an opposite orientation of its longitudinal and lateral magnetic poles, the distal tips of the two primary catheters can attach magnetically. As mentioned earlier, magnetic members in the mid-portion of the primary catheter can for example be in the form of electromagnets, providing a means of attachment of the distal tip of a secondary catheter to the mid-portion of a primary catheter, and this attachment mechanism provides an exemplary means for configuring a set of primary and secondary catheters as shown in FIG. 19. While the examples and attachment means described herein provides one method of magnetic attachment, other similar methods can be conceived and implemented by one skilled in the art by following the embodiments disclosed herein.

Figure 21:
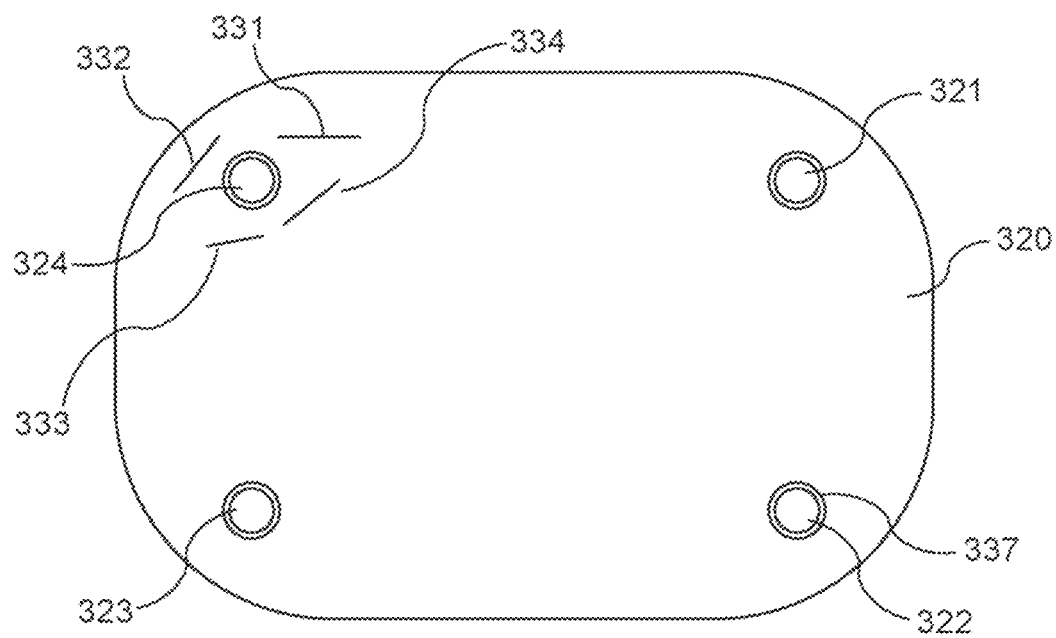
FIG. 21 is a schematic illustration of a two dimensional simulation model of a cardiac atrium, with four interior pulmonary vein "blood pool" regions disposed within a region representing the atrium, each pulmonary vein having an annular vessel wall region, and one of the pulmonary veins having four flat electrodes surrounding it, according to embodiments.

FIG. 21 shows an illustration of a two dimensional model of a cardiac atrium, with an atrial tissue region 320 that has interior "blood pool" regions 321, 322, 323 and 324. Each blood pool region represents a pulmonary vein and is surrounded by a thin annular such as for example the ring-shaped region 337 around pulmonary vein 322. Four electrodes 331, 332. 333 and 334 are shown disposed around pulmonary vein 324 so as to surround it. With a potential difference applied across some of the electrodes, simulation results can be obtained based on realistic values of electrical material properties for the various regions.

Figure 22:
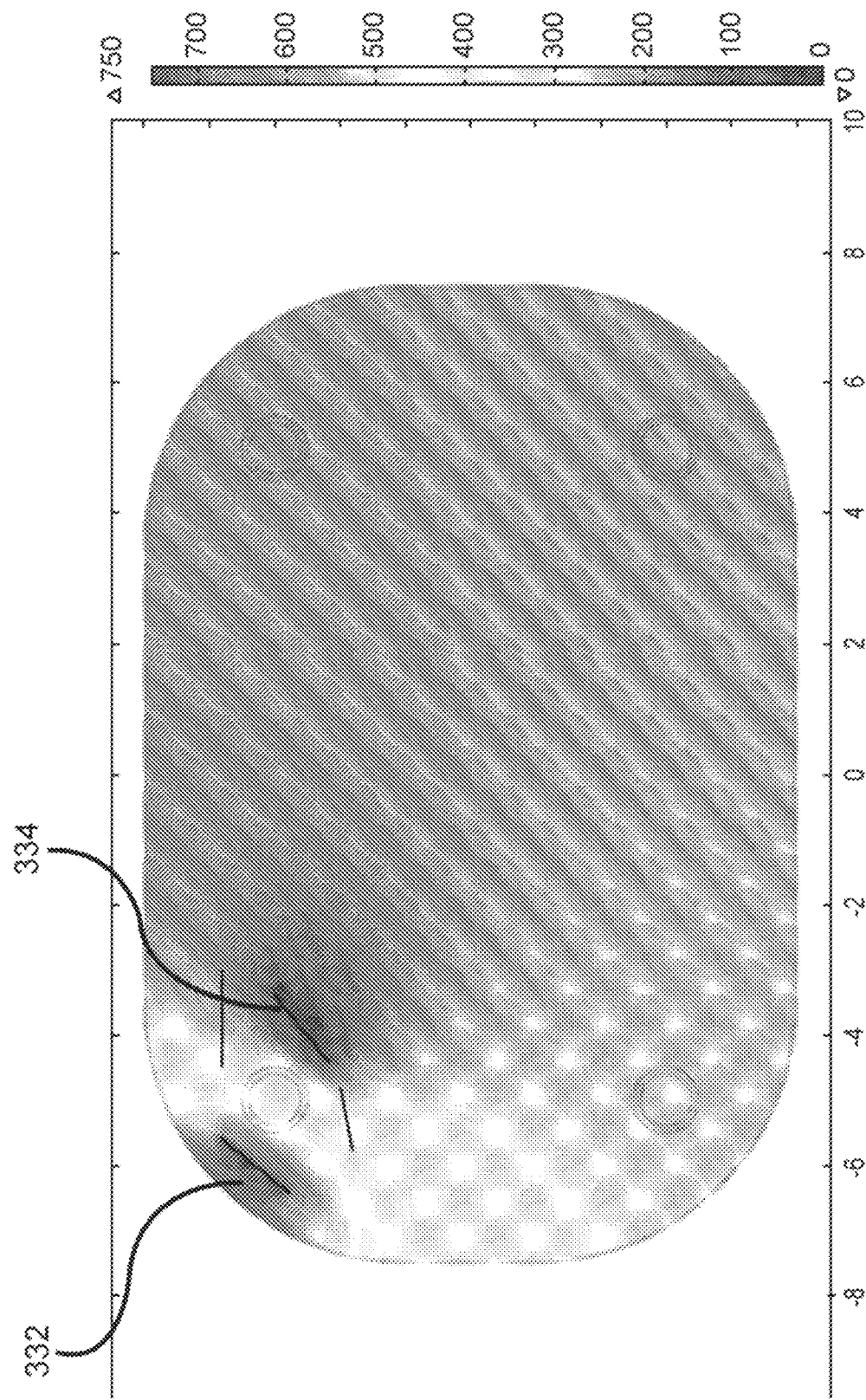
FIG. 22 is a simulation result in the form of a shaded contour plot of the electric potential, with a voltage difference set between two electrodes on opposite sides of a pulmonary vein, according to embodiments.
Figure 23:
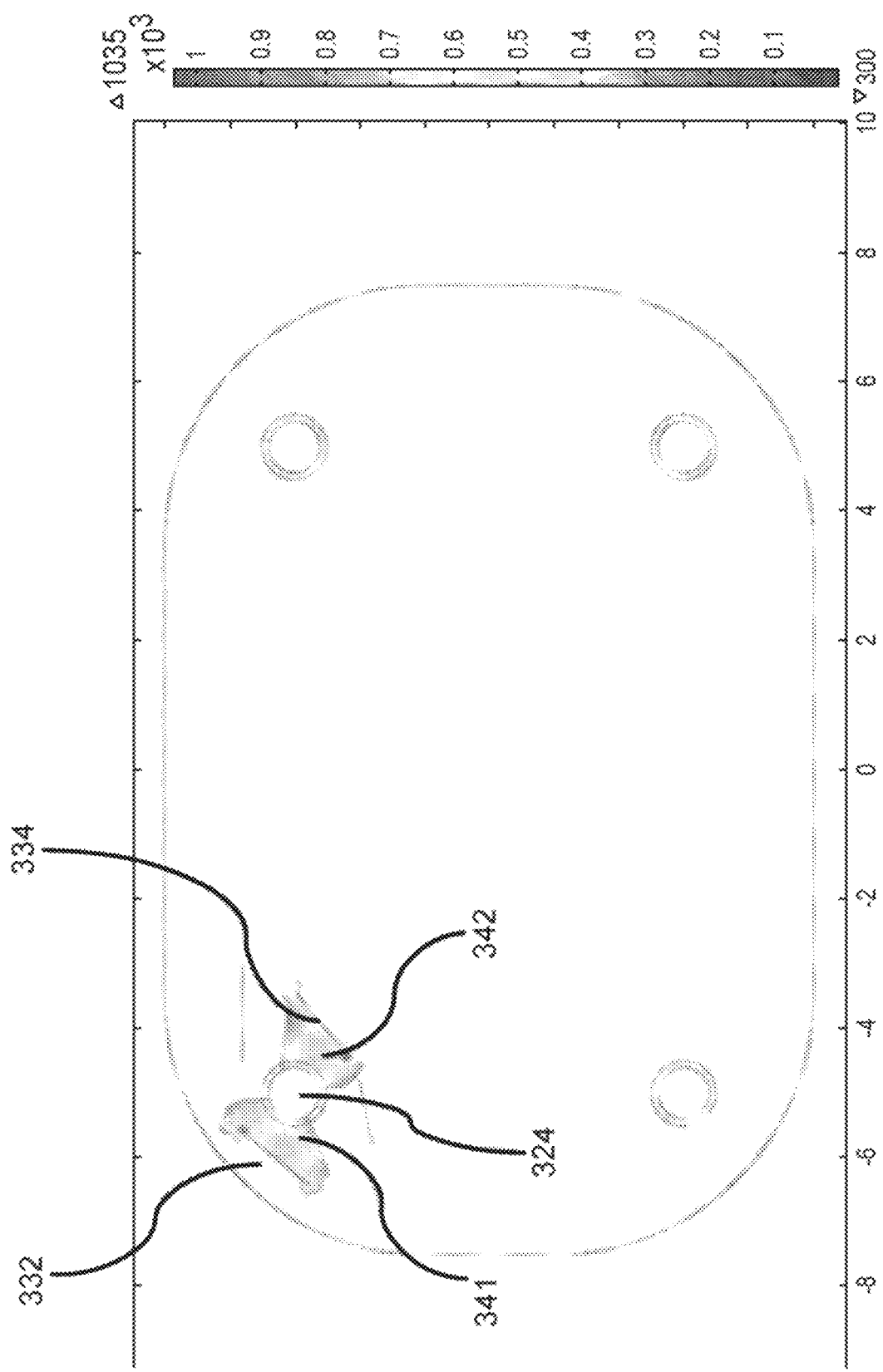
FIG. 23 is a simulation result corresponding to the situation in FIG. 6, in the form of a shaded contour plot of the electric field magnitude, with a voltage difference of 750 V between opposing electrodes around a pulmonary vein, according to embodiments.

A simulation result in the form of a shaded contour plot of the electric potential is shown in FIG. 22 for the case where a DC voltage is applied across a single anode electrode 332 and a single cathode electrode 334 on opposite sides of the blood pool region 324, with a potential difference of 750 V applied across anode and cathode. FIG. 23 shows the electric field intensity as a shaded contour plot where regions with an electric field strength of magnitude at least 200 V/cm (generally needed to cause irreversible electroporation ablation of myocytes) are indicated in the shaded areas. It is apparent that these ablated regions, indicated by region 341 around the anode electrode and region 342 around the cathode electrode, cover a significant fraction of a contour around pulmonary vein 324.

Figure 24:
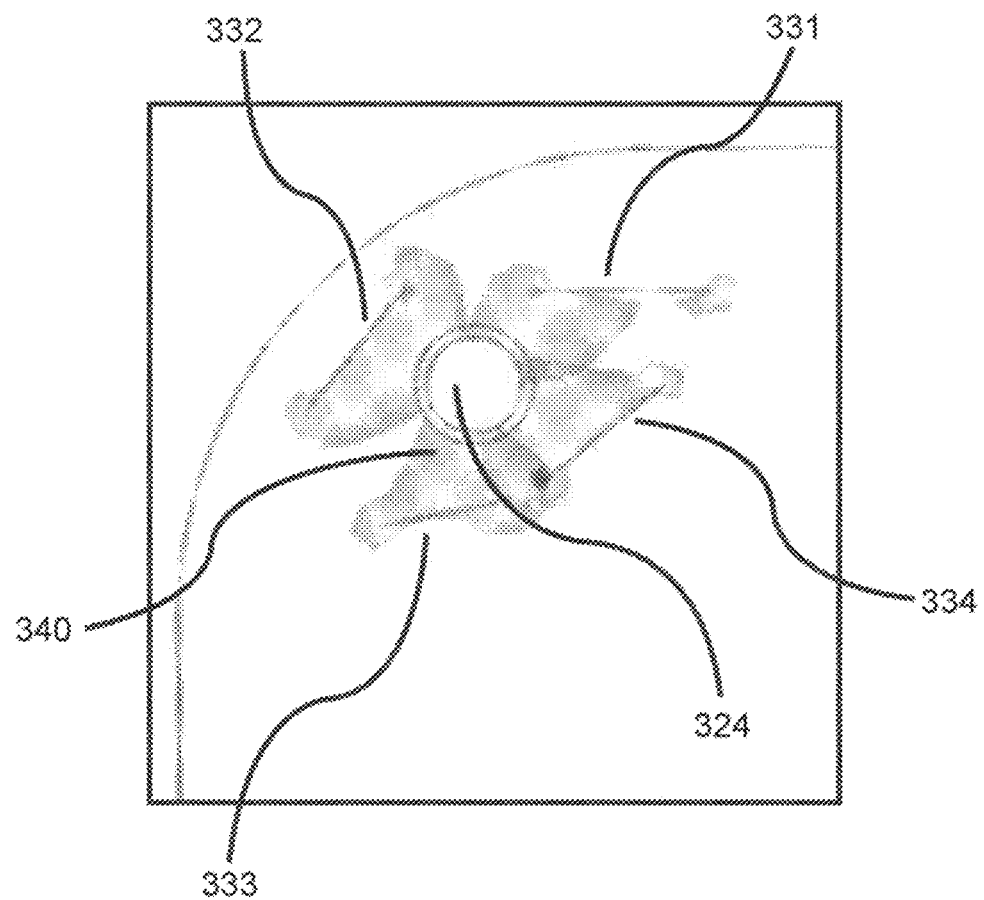
FIG. 24 is a simulation result corresponding to the situation in FIG. 6, in the form of a shaded contour plot of the electric field magnitude, with a voltage difference of 750 V between two pairs of opposing electrodes around a pulmonary vein, resulting in the entire peripheral region of the pulmonary vein being exposed to an electric field strength magnitude sufficient to generate irreversible electroporation, according to embodiments.

Likewise, for the case when electrodes 331 and 332 are set to be anode electrodes and electrodes 333 and 334 are defined to be cathode electrodes, with a potential difference of about 750 V applied across anode and cathode, FIG. 24 shows the electric field intensity as a shaded contour plot where regions with an electric field strength of magnitude at least about 200 V/cm are indicated in the shaded areas. It is apparent that in this case, the ablated region encompasses the entire contour around the pulmonary vein 324. Thus, the catheter devices with flexible electrodes, according to some embodiments, can be effectively utilized for rapid ablation therapy by the application of irreversible electroporation voltages. As can be seen from FIG. 24, the areas where electric field intensities are sufficiently large to generate irreversible electroporation occur substantially in the region between the electrodes, thus minimizing any potential damage to outer areas. Further, the applied voltage pulse level that is required to generate effective ablation can be significantly reduced; in the above simulation a voltage of about 750 V is seen to be sufficient to generate irreversible electroporation everywhere in a region of interest. This further enhances the safety of the procedure by reducing the likelihood of generating local electric fields that may be large enough to generate sparking or local dielectric breakdown as well as reduce the intensity of muscular contractions. The need for precise positioning of the electrodes is also reduced, leading to an overall faster therapeutic procedure.

Figure 25:
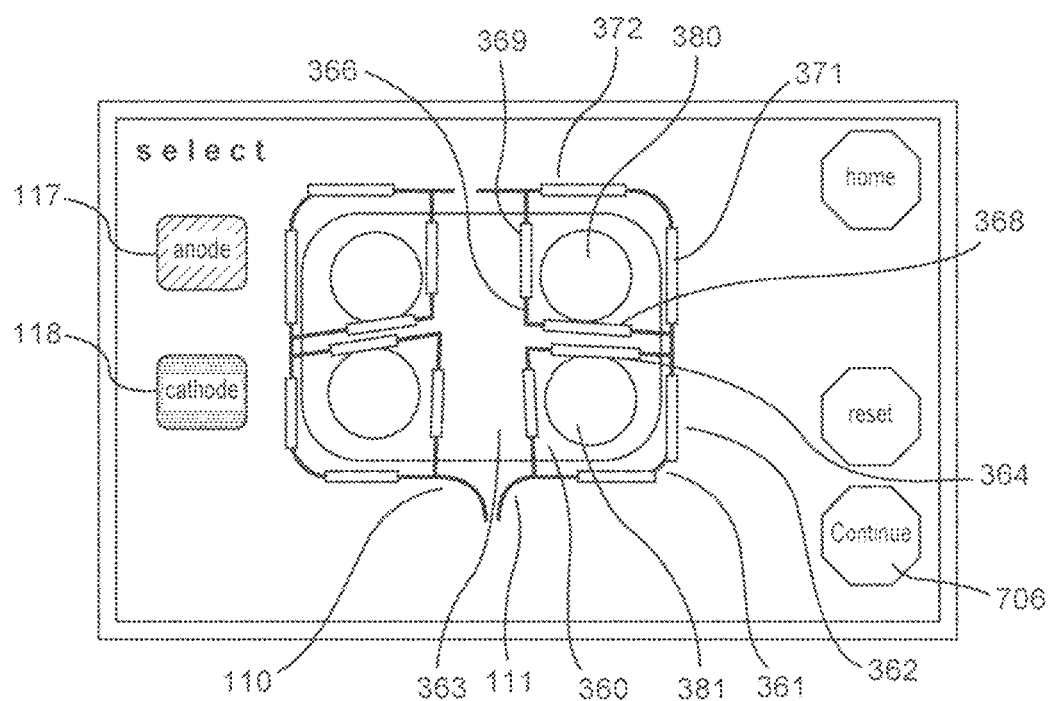
FIG. 25 is a schematic illustration of a user interface according to embodiments, showing electrodes on two primary catheters and electrodes on each of two secondary catheters passed through each primary catheter, and with the interface having buttons for selection or marking of anode electrode subsets and cathode electrode subsets.
Figure 26:
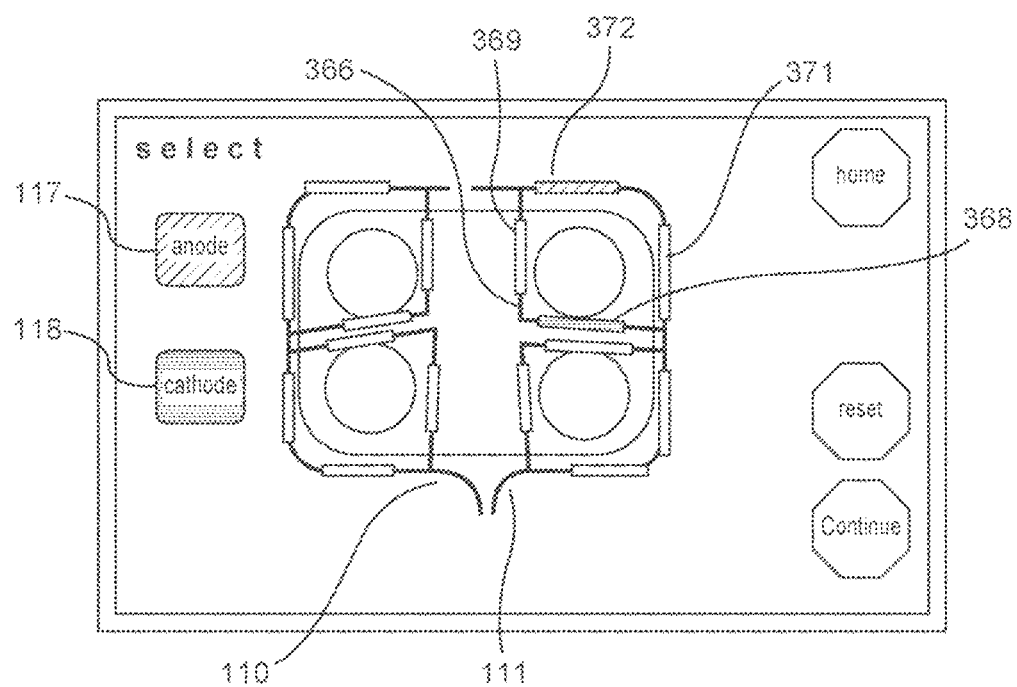
FIG. 26 is a schematic illustration of a user interface, according to embodiments, for selection of anode and cathode electrode subsets, showing a single selected anode electrode on one primary catheter device and a single selected cathode electrode on a secondary catheter device that is passed through the primary catheter device.

FIG. 25 shows a portion of a user interface of the electroporation system for selection (with graphical buttons 117 and 118) of anode and cathode electrodes, with two catheters connected to the system. The proximal leads of the two catheters (and thus the respective catheters themselves) are schematically indicated by 110 and 111, which each have four flexible electrodes. For example, the catheter 111 has flexible electrodes labeled 361, 362, 371 and 372 in FIG. 25. Secondary catheter 360 branches out from a proximal portion of catheter 111, while secondary catheter 366 branches out from a mid-portion of catheter 111. Secondary catheter 360 has flexible electrodes 363 and 364 respectively, while secondary catheter 366 has flexible electrodes 368 and 369 respectively. Electrodes 361, 362, 363 and 364 thus encircle the pulmonary vein labeled 381, while electrodes 368, 369, 372 and 371 encircle the pulmonary vein labeled 380.

Figure 17:
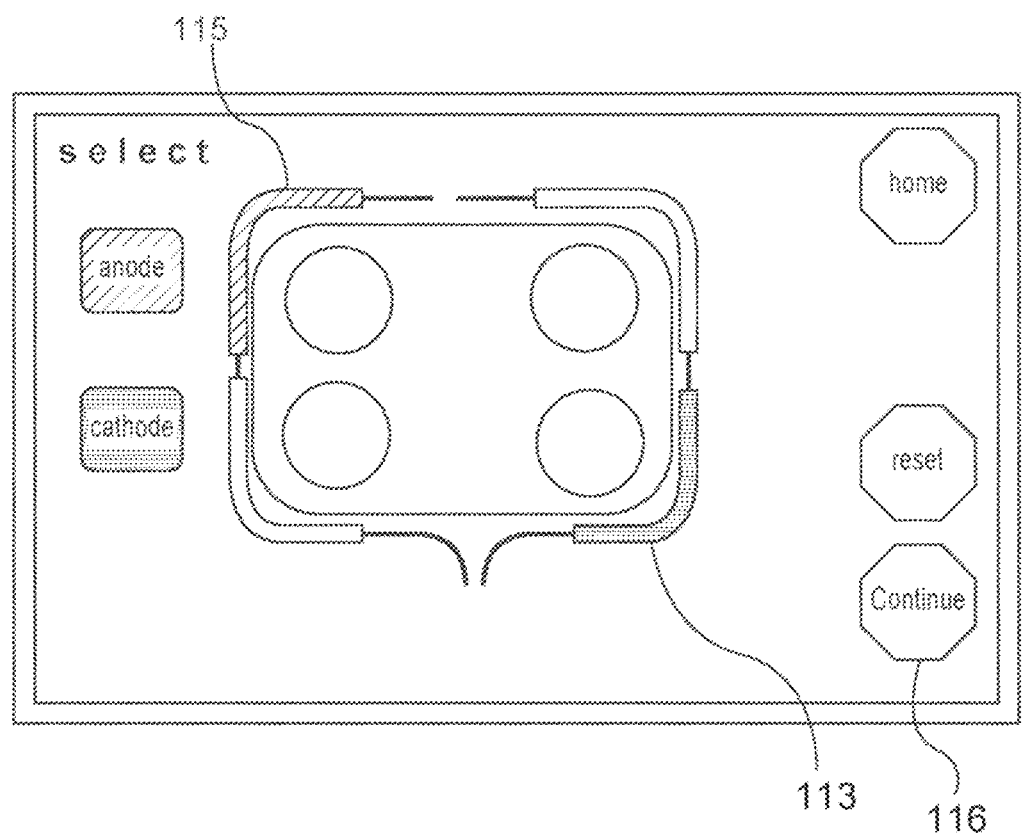
FIG. 17 is a schematic illustration of a user interface, according to embodiments, for selection of anode and cathode electrode subsets, showing a single selected anode electrode on one catheter device and a single selected cathode electrode on a second catheter device.

The buttons 117 and 118 can enable the selection of appropriate electrodes on the catheters as respectively anode or cathode with a "Continue" button 706. Once the selection is made, the appropriate electrodes are colored differently to indicate anode or cathode electrodes as shown in FIG. 17, where electrodes 372 and 368 have been marked respectively as anode electrode and cathode electrode, respectively on primary catheter 111 and secondary catheter 366. This selection has been shown for purely illustrative purposes. Other embodiments of user interface and mode of electrode selection can be implemented by one skilled in the art based on the teachings herein.

While various specific examples and embodiments of systems and tools for selective tissue ablation with irreversible electroporation were described in the foregoing for illustrative and exemplary purposes, it should be clear that a wide variety of variations and additional or alternate embodiments could be conceived or constructed by those skilled in the art based on the teachings disclosed herein. While specific methods of control and voltage application from a generator capable of selective excitation of sets of electrodes were disclosed, persons skilled in the art would recognize that any of a wide variety of other control or user input methods and methods of electrode subset selection etc. can be implemented without departing from the scope of the embodiments disclosed herein. Further, while some embodiments the voltage signals used in the ablation process are DC voltages or DC voltage pulses, in other embodiments the voltage signals can be AC voltages, or each voltage pulse can itself include time-varying components. Likewise, while the foregoing described a magnet-based scheme for positioning and attachment of catheters to each other, it should be apparent that other methods could be implemented for this purpose, including mechanical means using small manipulator arms or catches, pneumatically driven means, and so on, as can be conceived by those skilled in the art by employing the principles and teachings disclosed herein without departing from the scope of the embodiments disclosed herein.

Some embodiments described herein relate to a computer storage product with a non-transitory computer-readable medium (also referred to as a non-transitory processor-readable medium) having instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: flash memory, magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools.

What is claimed is:

1. A device, comprising:
   a primary catheter, including:
      one or more electrodes disposed in an intermediate portion of the primary catheter;
      one or more electrodes disposed in a distal portion of the primary catheter;
      two or more channels configured for passage of secondary catheters, each channel continuous from a proximal portion of the primary catheter to a lateral exit position on the primary catheter;
      a set of magnetic members including (1) one or more magnetic members disposed in the intermediate portion of the primary catheter and (2) a magnetic member disposed in the distal portion of the primary catheter;
   at least two secondary catheters configured for passage through the primary catheter, each secondary catheter including:
      one or more electrodes in its respective distal portion; and
      a magnetic member disposed in its respective distal portion and configured to releasably attach to one of the set of magnetic members of the primary catheter;
   for each electrode of the primary catheter and each electrode of the secondary catheter, an electrical lead attached to the corresponding electrode, each lead configured for, during use, being at an electrical voltage potential of at least 1 kV without resulting in dielectric breakdown across -the two or more channels of the primary catheter,
   wherein a geometric aspect ratio of at least one of the electrodes of the primary catheter is in the range between about 3 and about 20.

2. The device of claim 1, wherein:
   the primary catheter includes a shaft including a plurality of stepped sections separated by gaps along a length of the primary catheter, and
   each of the electrodes of the primary catheter located at a different stepped section of the plurality of stepped sections of the shaft.

3. The device of claim 2, wherein the shaft at each stepped section of the plurality of stepped sections has an outer diameter that is less than an outer diameter of the shaft at the gaps.

4. The device of claim 2, wherein the gaps between adjacent electrodes of the electrodes of the primary catheter are between about 2 mm and about 12 mm.

5. The device of claim 1, wherein at least one of the electrodes of the primary catheter includes a coiled length of an electrical conductor.

6. The device of claim 1, the shaft further including a lumen formed therein such that the primary catheter is, configured for, when a guidewire is disposed in the lumen during use, movement along the guidewire.

7. The device of claim 1, wherein a geometric aspect ratio of at least one electrode of one of the secondary catheters is in the range between about 3 and about 20.

8. The device of claim 1, wherein the magnetic member disposed in the distal portion of the primary catheter includes one magnetic pole oriented substantially longitudinally and one magnetic pole oriented substantially laterally with respect to an elongate axis of the primary catheter.

9. The device of claim 1, wherein the one or more magnetic members disposed in the intermediate portion of the primary catheter includes an electromagnet.

10. The device of claim 1, further comprising a lumen configured for, during use, introducing the device over a guidewire.

11. The device of claim 1, wherein the magnetic member disposed in at least one secondary catheter includes magnetizable material.

12. The device of claim 1, wherein each electrode of a set of the electrodes of the primary catheter includes a set of conducting rings separated by spaces and disposed along the primary catheter, the set of conducting rings of each electrode of the set of electrodes electrically connected together so as to electrically define a common electrical potential for the each electrode, the primary catheter including gaps configured for separating adjacent electrodes of the set of electrodes.

13. The device of claim 12, wherein a width of each conducting ring of the set of conducting rings of each electrode of the set of flexible electrodes is in the range between about 0.5 mm and about 6 mm.

14. The device of claim 13, wherein the width of adjacent conducting rings of the set of conducting rings of each electrode of the set of electrodes is different.

15. The device of claim 12, wherein the space between adjacent conducting rings of the set of conducting rings of each electrode of the set of electrodes is in the range between about 1 mm and about 4 mm.

16. The device of claim 12, wherein the gaps between adjacent electrodes of the set of electrodes are between about 2 mm and about 12 mm.

17. The device of claim 1, wherein the electrodes of the primary catheter and the electrodes of the secondary catheter are configured to generate an electric field with sufficient intensity to cause irreversible electroporation of tissue.

* * * * *